(12) United States Patent
Guo et al.

(10) Patent No.: US 11,573,219 B2
(45) Date of Patent: Feb. 7, 2023

(54) LC/MS/MS ANALYSIS FOR MEAT SPECIATION IN RAW AND PROCESSED MEAT PRODUCT

(71) Applicant: DH Technologies Development Pte. Ltd., Singapore (SG)

(72) Inventors: Lihai Guo, Beijing (CN); Huafen Liu, San Jose, CA (US); Stephen Lock, Pudsey (GB); Si Mou, San Mateo, CA (US); PeiBin Qin, Beijing (CN); Lei Xiong, San Jose, CA (US)

(73) Assignee: DH Technologies Development Pte. Ltd., Singapore (SG)

( * ) Notice: Subject to any disclaimer, the term of this patent is extended or adjusted under 35 U.S.C. 154(b) by 907 days.

(21) Appl. No.: 16/331,699

(22) PCT Filed: Sep. 7, 2017

(86) PCT No.: PCT/IB2017/055395
§ 371 (c)(1),
(2) Date: Mar. 8, 2019

(87) PCT Pub. No.: WO2018/047091
PCT Pub. Date: Mar. 15, 2018

(65) Prior Publication Data
US 2019/0360987 A1    Nov. 28, 2019

Related U.S. Application Data

(60) Provisional application No. 62/384,925, filed on Sep. 8, 2016.

(51) Int. Cl.
*G01N 33/12* (2006.01)
*G01N 30/72* (2006.01)
*G01N 30/88* (2006.01)
*G01N 33/68* (2006.01)
*H01J 49/00* (2006.01)

(52) U.S. Cl.
CPC ......... *G01N 33/12* (2013.01); *G01N 30/7233* (2013.01); *G01N 30/88* (2013.01); *G01N 33/6848* (2013.01); *G01N 2030/8813* (2013.01); *H01J 49/004* (2013.01)

(58) Field of Classification Search
None
See application file for complete search history.

(56) References Cited

U.S. PATENT DOCUMENTS

2016/0086782 A1    3/2016   Lock

OTHER PUBLICATIONS

Montowska, M. et al. Rapid Detection of Peptide Markers for Authentication Purposes in Raw and Cooked Meat Using Ambient Liquid Extraction Surface Analysis Mass Spectrometry, Analytical Chemistry, 86, 10257-10265 (Year: 2014).*
International Search Report and Written Opinion for PCT/IB2017/055395 dated Dec. 28, 2017.
Von Bargen, Christoph et al., "New Sensitive high-performance liquid chromatography-tandem mass spectrometry method for the detection of horse and pork in halal beef" Journal of Agricultural and Food Chemistry, Nov. 22, 2013, vol. 61, pp. 11986-11994 and Supplementary material. See abstract; p. 11987; table 1; and supplementary table 5.

(Continued)

*Primary Examiner* — Xiaoyun R Xu

(57) ABSTRACT

Apparatus, methods and kits for detecting the contamination of a meat sample with another type of meat using parent-daughter ion transition monitoring that identifies peptides specific to a particular type of meat. The meat types detected can include pork, beef, lamb, chicken, duck and/or horse and one or more combinations thereof.

3 Claims, 14 Drawing Sheets

Specification includes a Sequence Listing.

(56) References Cited

OTHER PUBLICATIONS

Mai, Huijuan et al., "Characterization of cosmetic sticks at Xiaohe Cemetery in early Bronze Age Xinjiang, China", Scientific Reports, Jan. 28, 2016, vol. 6, Article No. 18939, internal pp. 1-9. See table 1.

Marbaix, Helene et al., "Identification of proteins and peptide biomarkers for detecting banned Processed Animal Proteins (PAPs) in meat and bone meal by mass spectrometry", Journal of Agricultural and Food Chemistry, Mar. 4, 2016, vol. 64, pp. 2405-2414. See abstract; and table 5.

Claydon, Amy J. et al., Identification of novel peptides for horse meat speciation in highly processed foodstuffs, Food Additives & Contaminants: Part A, 2015, vol. 32, No. 10, pp. 1718-1729 See p. 1718; and table 4.

Zeng, Tao et al., "Comparative proteomic analysis of the hepatic response to heat stress in Muscovy and Pekin ducks; insight into thermal tolerance related to energy metabolism", PloS one, Oct. 7, 2013, vol. 8, Issue 10, eNo. e76917, internal pp. 1-17 See abstract; and table 2.

Miguel A. Sentandreu, "A Proteomic-Based Approach for Detection of Chicken in Meat Mixes", Journal of Proteome Research, V9, pp. 3374-3383, May 3, 2010.

Atiya Abbasi, "Molecular Basis of Bird Respiration: Primary Hemoglobin Structure Component from Tufted Duck (*Aythya fuligula*,Anseriformes)—Role of alpha99Arg in Formation of a Complex Salt Bridge Network", Biochemical and Biophysical Research Communications, V291 pp. 176-184, 2002.

Yingyi Zhang, "Analysis of nitrated proteins and tryptic peptides by HPLC-chip-MS/MS: site-specific quantification, nitration degree, and reactivity of tyrosine residues", Anal Bioanal Chem, V399, pp. 459-471, Nov. 7, 2011.

\* cited by examiner

```
                         SEQUENCE LISTING

<160> NUMBER OF SEQ ID NOS: 24

<210> SEQ ID NO 1
    <211> LENGTH: 16
    <212> TYPE: PRT
    <213> ORGANISM: Sus scrofa

<400> SEQUENCE: 1

Ser Leu Tyr Ser Ser Ala Glu Asn Glu Pro Pro Val Pro Leu Val Arg
    1               5                   10                  15

<210> SEQ ID NO 2
    <211> LENGTH: 9
    <212> TYPE: PRT
    <213> ORGANISM: Sus scrofa

<400> SEQUENCE: 2

Gly Gly Pro Leu Thr Ala Ala Tyr Arg
    1               5

<210> SEQ ID NO 3
    <211> LENGTH: 11
    <212> TYPE: PRT
    <213> ORGANISM: Sus scrofa

<400> SEQUENCE: 3

Ser Ala Leu Ala His Ala Val Gln Ser Ser Arg
    1               5                   10

<210> SEQ ID NO 4
    <211> LENGTH: 9
    <212> TYPE: PRT
    <213> ORGANISM: Sus scrofa
```

```
<400> SEQUENCE: 4

Thr Leu Ala Phe Leu Phe Ala Glu Arg
1               5

<210> SEQ ID NO 5
<211> LENGTH: 10
<212> TYPE: PRT
<213> ORGANISM: Bos taurus

<400> SEQUENCE: 5

Leu Val Asn Glu Leu Thr Glu Phe Ala Lys
1               5                   10

<210> SEQ ID NO 6
<211> LENGTH: 8
<212> TYPE: PRT
<213> ORGANISM: Bos taurus

<400> SEQUENCE: 6

Ala Glu Phe Val Glu Val Thr Lys
1               5

<210> SEQ ID NO 7
<211> LENGTH: 10
<212> TYPE: PRT
<213> ORGANISM: Bos taurus

<400> SEQUENCE: 7

Thr Leu Glu Asp Gln Val Asn Glu Leu Lys
1               5                   10

<210> SEQ ID NO 8
<211> LENGTH: 16
<212> TYPE: PRT
<213> ORGANISM: Bos taurus

<400> SEQUENCE: 8

Val Glu Leu Pro Ser Leu Ile Pro Val Ile Leu Glu Lys Pro Ala Lys
1               5                   10                  15

<210> SEQ ID NO 9
<211> LENGTH: 15
<212> TYPE: PRT
<213> ORGANISM: Ovis aries

<400> SEQUENCE: 9

Val Gly Gly Asn Ala Gly Ala Tyr Gly Ala Glu Ala Leu Glu Arg
1               5                   10                  15

<210> SEQ ID NO 10
<211> LENGTH: 16
<212> TYPE: PRT
<213> ORGANISM: Ovis aries

<400> SEQUENCE: 10

His His Gly Asn Glu Phe Thr Pro Val Leu Gln Ala Asp Phe Gln Lys
1               5                   10                  15

<210> SEQ ID NO 11
<211> LENGTH: 13
<212> TYPE: PRT
<213> ORGANISM: Ovis aries
```

<400> SEQUENCE: 11

Leu Leu Gly Ser Leu Asp Ile Asp His Asn Gln Tyr Arg
1               5                   10

<210> SEQ ID NO 12
<211> LENGTH: 12
<212> TYPE: PRT
<213> ORGANISM: Ovis aries

<400> SEQUENCE: 12

Leu Thr Gly Gly Val Met His Tyr Gly Asn Leu Lys
1               5                   10

<210> SEQ ID NO 13
<211> LENGTH: 14
<212> TYPE: PRT
<213> ORGANISM: Gallus gallus

<400> SEQUENCE: 13

Leu Ser Val Glu Ala Leu Asn Ser Leu Glu Gly Glu Phe Lys
1               5                   10

<210> SEQ ID NO 14
<211> LENGTH: 8
<212> TYPE: PRT
<213> ORGANISM: Gallus gallus

<400> SEQUENCE: 14

Val Leu Thr Pro Glu Leu Tyr Lys
1               5

<210> SEQ ID NO 15
<211> LENGTH: 11
<212> TYPE: PRT
<213> ORGANISM: Gallus gallus

<400> SEQUENCE: 15

Met Thr Glu Glu Glu Val Glu Glu Leu Met Lys
1               5                   10

<210> SEQ ID NO 16
<211> LENGTH: 14
<212> TYPE: PRT
<213> ORGANISM: Gallus gallus

<400> SEQUENCE: 16

Ile Val Glu Ser Met Gln Ser Thr Leu Asp Ala Glu Val Arg
1               5                   10

<210> SEQ ID NO 17
<211> LENGTH: 11
<212> TYPE: PRT
<213> ORGANISM: Anas platyrhynchos

<400> SEQUENCE: 17

Met Thr Glu Glu Glu Val Asp Glu Leu Met Lys
1               5                   10

<210> SEQ ID NO 18
<211> LENGTH: 21
<212> TYPE: PRT
<213> ORGANISM: Anas platyrhynchos

```
<400> SEQUENCE: 18

Thr Leu Ala Leu Leu Phe Ala Asn Tyr Gly Gly Ala Asp Ala Glu Ala
1               5                   10                  15

Gly Gly Gly Gly Lys
            20

<210> SEQ ID NO 19
<211> LENGTH: 21
<212> TYPE: PRT
<213> ORGANISM: Anas platyrhynchos

<400> SEQUENCE: 19

Val Ala Ala Ala Leu Val Glu Ala Val Asn His Ile Asp Asp Ile Ala
1               5                   10                  15

Gly Ala Leu Ser Lys
            20

<210> SEQ ID NO 20
<211> LENGTH: 9
<212> TYPE: PRT
<213> ORGANISM: Anas platyrhynchos

<400> SEQUENCE: 20

Met Phe Leu Ala Tyr Pro Gln Thr Lys
1               5

<210> SEQ ID NO 21
<211> LENGTH: 9
<212> TYPE: PRT
<213> ORGANISM: Equus caballus

<400> SEQUENCE: 21

Leu Val Asn Asp Leu Thr Gly Gln Arg
1               5

<210> SEQ ID NO 22
<211> LENGTH: 19
<212> TYPE: PRT
<213> ORGANISM: Equus caballus

<400> SEQUENCE: 22

Thr Leu Ala Leu Leu Phe Ser Gly Pro Ala Ser Ala Asp Ala Glu Ala
1               5                   10                  15

Gly Gly Lys

<210> SEQ ID NO 23
<211> LENGTH: 14
<212> TYPE: PRT
<213> ORGANISM: Equus caballus

<400> SEQUENCE: 23

Val Val Glu Thr Met Gln Thr Met Leu Asp Ala Glu Ile Arg
1               5                   10

<210> SEQ ID NO 24
<211> LENGTH: 10
<212> TYPE: PRT
<213> ORGANISM: Equus caballus

<400> SEQUENCE: 24

Glu Phe Glu Ile Gly Asn Leu Gln Ser Lys
1               5                   10
```

LC/MS/MS ANALYSIS FOR MEAT SPECIATION IN RAW AND PROCESSED MEAT PRODUCT

RELATED APPLICATIONS

This application claims the benefit of priority from U.S. Provisional Application Ser. No. 62/384,925, filed on Sep. 8, 2016, the entire content of which is incorporated by reference herein.

FIELD

This relates to the analysis and identification of contamination in meat samples.

BACKGROUND

The Food Standards Agency (FSA), an independent government department of the United Kingdom, announced in January of 2013 that deoxyribonucleic acid (DNA) molecules of horse and/or pig had been identified in beef products sold by several supermarket chains. Follow-up testing across Europe and beyond has revealed widespread incidences of such contamination. General concerns have been raised about the presence of other species of meat in supposedly pure samples of a particular meat product. The contamination can be a result of the presence of an undesired amount of one or more of pork, beef, lamb, chicken, duck and/or horse in the meat product.

However, most existing testing methods are based on detection of a species'-specific DNA in meat, using the polymerase chain reaction (PCR)—which is time consuming and does not detect or identify proteins. This is a concern because DNA can be easily disrupted or removed during standard meat processing and food manufacturing. As a result, horse tissue or other contaminants remain undetected in food samples, despite strong presence of the contaminating proteins. An alternative protein-based method, enzyme-linked immunosorbent assay (ELISA), can be used to complement the DNA testing. However, the ELISA method detects only one part of the protein and not multiple protein markers.

Several methods of detecting potential meat contamination have been suggested. U.S. Pat. No. 9,373,486, published on Jun. 21, 2016 and incorporated by reference, herein, teaches an MRM-initiated detection and sequencing (MIDAS) workflow for detecting meat contamination. Anal. Chem. 2015 87 10315-10322, the contents of which are incorporated by reference herein, describes a MRM based technique that focuses on the detection of myoglobin derived peptides to detect the presence of undeclared meats which include horse, beef, pork and lamb. As indicated in this reference, not all peptides from a given animal are useful as markers due to such issues as lack of signal quality, non-uniqueness between differing species, etc.

There is a need in the art for a simplified manner to reliably detect the presence of meat contamination of pork, beef, lamb, chicken, duck and/or horse in meat samples.

SUMMARY

According to various embodiments of the present teachings, a method of identifying the presence of one or more different species of meat in one or more samples is described that doesn't require chemical labeling. In various embodiments, the method comprises identifying the presence of one or more different species of meat in a sample using parent-daughter ion transition monitoring (PDITM). In various embodiments, the method can be used to identify the presence of one or more of pork, beef, lamb, chicken, duck and/or horse in a meat sample. Tryptic peptides unique to each species can be observed using liquid chromatography-tandem mass spectrometry (LC-MS/MS) and the parent-daughter ion transitions that are herein described.

The term "parent-daughter ion transition monitoring" or "PDITM" refers to, for example, a measurement using mass spectrometry whereby the transmitted mass-to-charge (m/z) range of a first mass separator (often referred to as the first dimension of mass spectrometry and can be described as Q1) is selected to transmit a molecular ion (often referred to as "the parent ion" or "the precursor ion") to an ion fragmentor (e.g. a collision cell, photodissociation region, etc.) to produce fragment ions (often referred to as "daughter ions") and the transmitted m/z range of a second mass separator (often referred to as the second dimension of mass spectrometry and can be described as Q3) is selected to transmit one or more daughter ions to a detector which measures the daughter ion signal. The combination of parent ion and daughter ion masses monitored can be referred to as the "parent-daughter ion transition" monitored or as the precursor-daughter ion transition. The daughter ion signal at the detector for a given parent ion-daughter ion combination monitored can be referred to as the "parent-daughter ion transition signal". In various embodiments of the present teachings, the parent ion is a peptide sequence derived from a protein that is unique to a species of an animal and that the parent-daughter ion transition being monitored is unique to that animal.

For example, one embodiment of parent-daughter ion transition monitoring is multiple reaction monitoring (MRM) (also referred to as selective reaction monitoring). In various embodiments of MRM, the monitoring of a given parent-daughter ion transition comprises using as the first mass separator (e.g., a first quadrupole parked on the parent ion m/z of interest) to transmit the parent ion of interest and using the second mass separator (e.g., a second quadrupole parked on the daughter ion m/z of interest) to transmit one or more daughter ions of interest. In various embodiments, a PDITM can be performed by using the first mass separator (e.g., a quadrupole parked on a parent ion m/z of interest) to transmit parent ions and scanning the second mass separator over a m/z range including the m/z value of the one or more daughter ions of interest.

For example, a tandem mass spectrometer (MS/MS) instrument or, more generally, a multidimensional mass spectrometer ($MS^n$) instrument, can be used to perform PDITM, e.g., MRM.

Examples of suitable mass analyzer systems include, but are not limited to, those that comprise one or more of a triple quadrupole, a quadrupole-linear ion trap, a quadrupole Time of Flight (TOF), and a TOF-TOF.

In some embodiments, methods of detecting the contamination of a beef sample by one or more meats selected from the group consisting of pork, lamb, chicken and duck is described. The method comprising: adding a proteolytic enzyme to the sample to lyse at least a portion of any of the one or more meats other than beef in the sample, into a plurality of peptides; and utilizing liquid chromatography tandem mass spectrometry (LC-MS/MS) to analyze said plurality of peptides to determine whether the one or more meats other than beef is present by monitoring at least one parent-daughter ion pair transition with specified m/z value associated with a specific amino acid sequence selected from Tables 1, 2, 4, and 5 referred to below.

In some embodiments, a method of detecting pork in a sample is disclosed. The method comprising:
adding a proteolytic enzyme to the sample to lyse at least a portion of any pork in the sample, into a plurality of peptides; and utilizing liquid chromatography tandem mass spectrometry (LC-MS/MS) to analyze said plurality of peptides to determine whether the pork is present by monitoring at least one parent-daughter ion pair transition with specified m/z value associated with a specific amino acid sequence selected from Table 1.

In some embodiments, a method of detecting beef in a sample is described. The method comprising:
adding a proteolytic enzyme to the sample to lyse at least a portion of any beef in the sample, into a plurality of peptides; and utilizing liquid chromatography tandem mass spectrometry (LC-MS/MS) to analyze said plurality of peptides to determine whether the beef is present by monitoring at least one parent-daughter ion pair transition with specified m/z value associated with a specific amino acid sequence selected from Table 2.

In some embodiments, a method of detecting lamb in a sample is described. The method comprising:
adding a proteolytic enzyme to the sample to lyse at least a portion of any lamb in the sample, into a plurality of peptides; and utilizing liquid chromatography tandem mass spectrometry (LC-MS/MS) to analyze said plurality of peptides to determine whether the lamb is present by monitoring at least one parent-daughter ion pair transition with specified m/z value associated with a specific amino acid sequence selected from Table 3.

In some embodiments, a method of detecting chicken in a sample is described. The method comprising:
adding a proteolytic enzyme to the sample to lyse at least a portion of any chicken in the sample, into a plurality of peptides; and utilizing liquid chromatography tandem mass spectrometry (LC-MS/MS) to analyze said plurality of peptides to determine whether the chicken is present by monitoring at least one parent-daughter ion pair transition with specified m/z value associated with a specific amino acid sequence selected from Table 4.

In some embodiments, a method of detecting duck in a sample is described. The method comprising:
adding a proteolytic enzyme to the sample to lyse at least a portion of any duck in the sample, into a plurality of peptides; and utilizing liquid chromatography tandem mass spectrometry (LC-MS/MS) to analyze said plurality of peptides to determine whether the duck is present by monitoring at least one parent-daughter ion pair transition with specified m/z value associated with a specific amino acid sequence selected from Table 5.

In some embodiments, a method of detecting horse in a sample is described. The method comprising:
adding a proteolytic enzyme to the sample to lyse at least a portion of any horse in the sample, into a plurality of peptides; and utilizing liquid chromatography tandem mass spectrometry (LC-MS/MS) to analyze said plurality of peptides to determine whether the horse is present by monitoring at least one parent-daughter ion pair transition with specified m/z value associated with a specific amino acid sequence selected from Table 6.

In some embodiments, a system for detecting pork, beef, lamb, chicken, duck and horse meat is described. The method comprising: a tandem mass spectrometer configured to perform parent-daughter ion transition monitoring; and a processor in communication with the tandem mass spectrometer that sends instructions to the tandem mass spectrometer to detect the presence of peptides unique to pork, beef, lamb, chicken, duck and/or horse by monitoring one or more parent-daughter ion transitions selected from Tables 1-6.

BRIEF DESCRIPTION OF THE DRAWINGS

The skilled artisan will understand that the drawings, described below, are for illustration purposes only. The drawings are not intended to limit the scope of the present teachings in any way.

Figure 1:
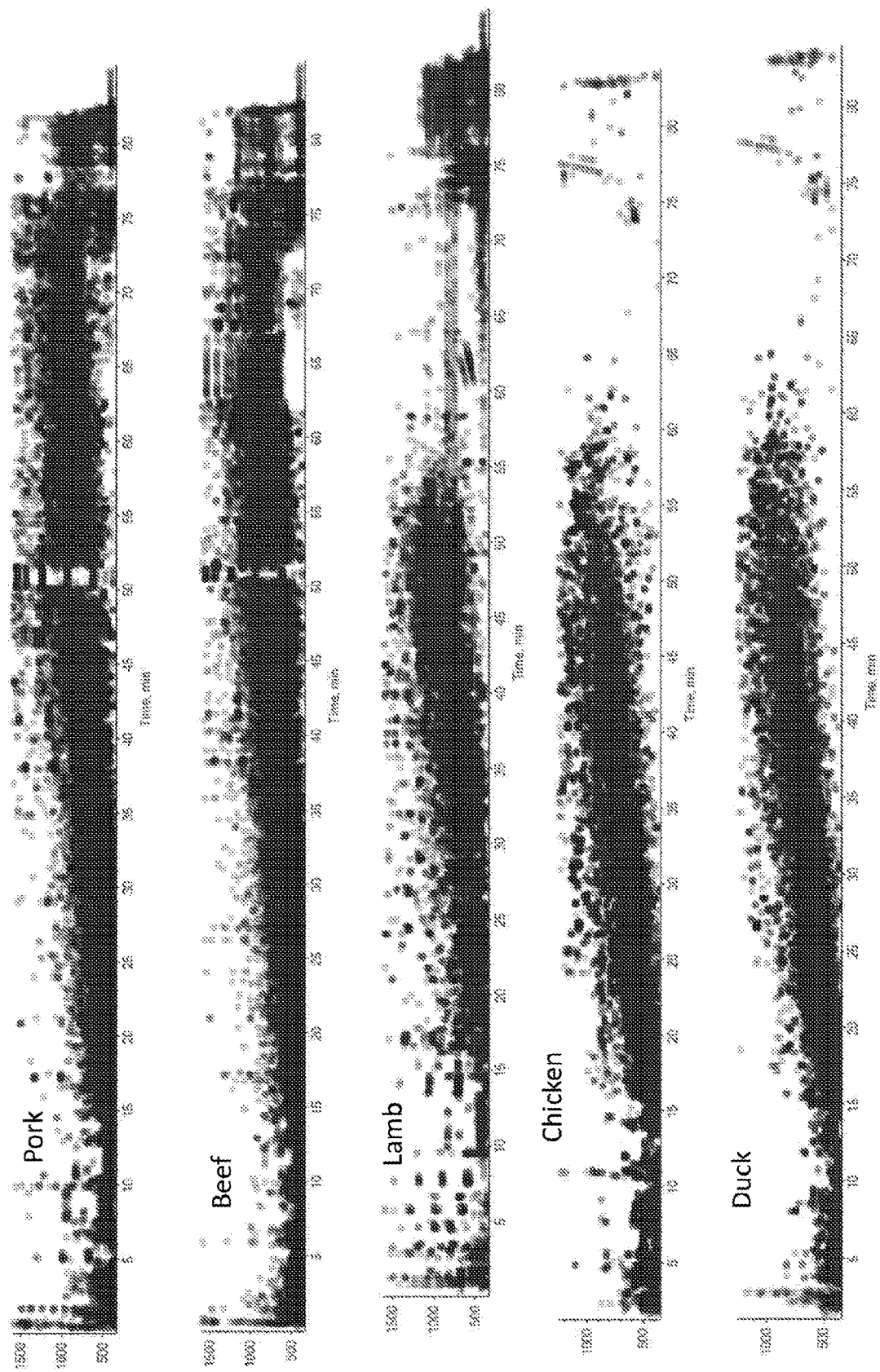
FIG. 1 depicts a representation of the number of precursor ions detected in a pure sample of a particular type of meat seen over the course of an LC run.

Before one or more embodiments of the invention are described in detail, one skilled in the art will appreciate that the invention is not limited in its application to the details of construction, the arrangements of components, and the arrangement of steps set forth in the following detailed. The invention is capable of other embodiments and of being practiced or being carried out in various ways. Also, it is to be understood that the phraseology and terminology used herein is for the purpose of description and should not be regarded as limiting.

DETAILED DESCRIPTION OF PREFERRED EMBODIMENTS

Those skilled in the art will understand that the methods and kits described herein are non-limiting exemplary embodiments and that the scope of the applicants' disclosure is defined solely by the claims. While the applicant's teachings are described in conjunction with various embodiments, it is not intended that the applicant's teachings be limited to such embodiments. On the contrary, the applicant's teachings encompass various alternatives, modifications, and equivalents, as will be appreciated by those of skill in the art. The features illustrated or described in connection with one exemplary embodiment may be combined with the features of other embodiments. Such modifications and variations are intended to be included within the scope of the applicants' disclosure.

According to various embodiments, methods are provided for screening a sample for the presence or quantity of pork, beef, lamb, chicken, duck and/or horse in meat samples using mass spectrometry by detecting one or more amino acid sequences specific to the meat of interest. For example, an animal specific peptide unique to a particular animal can be detected using Liquid Chromatography-Tandem Mass Spectrometry (LC-MS/MS). Selected MRM transitions can be observed for each peptide to enable the detection and/or quantitation of the type of meat in the sample.

The methods can utilize a variety of mass spectrometry techniques known in the art. For example, the mass spectrometry technique can be a tandem mass spectrometry (MS/MS) technique and/or a liquid chromatography tandem mass spectrometry (LC-MS/MS) technique. In some embodiments, the technique comprises an LC-MS/MS technique and the use of a triple quadrupole instrument and Multiple Reaction Monitoring (MRM). In the within teachings the term "about" as used herein in reference to precursor-product ion pair transitions is intended to mean within a range of +/−one (1) atomic mass unit.

According to some embodiments, the method can comprise detecting and/or quantifying pork in the sample by detecting at least one isolated peptide specific to pork, for example, one or more of the peptides having an amino acid sequence of SEQ ID NOS: 1-4 identified herein. For example, LC-MS/MS can be used to determine the presence and/or quantity of pork-specific peptides in the sample. In one exemplary embodiment, a triple quadrupole mass spectrometer can be used to monitor selected Multiple Reaction Monitoring (MRM) transitions. In some embodiments, the pork-specific peptide can have the amino acid sequence of SEQ ID NO: 1 identified herein, and the method can include monitoring at least one parent-daughter ion pair transition having an m/z value of about 453/581 or 453/480. In other embodiments, the pork-specific peptide can have the amino acid sequence of SEQ ID NO: 2 identified herein, and the method can include monitoring at least one parent-daughter ion pair transition having an m/z value of about 879/777 or 879/981. In other embodiments, the pork-specific peptide can have the amino acid sequence of SEQ ID NO: 3 identified herein, and the method can include monitoring at least one parent-daughter ion pair transition having an m/z value of about 564/784 or 564/393. In other embodiments, the pork-specific peptide can have the amino acid sequence of SEQ ID NO: 4, and the method can include monitoring at least one parent-daughter ion pair transition having an m/z value of about 534/853 or 534/782.

In one exemplary embodiment, the method can include monitoring multiple parent-daughter ion pair transitions associated with each pork-specific peptide. By way of example, the pork-specific peptide having the amino acid sequence of SEQ ID NO: 1 can be identified by monitoring one or both of the parent-daughter ion pair transitions having an m/z value of about 453/581 or 453/480.

In one embodiment, the method for detecting or quantifying pork in the sample can include detecting multiple pork-specific peptides. By way of non-limiting example, pork can be detected and/or quantified by using any combination, or all, of the peptides having the amino acid sequences of SEQ ID NOS: 1-4 identified herein. As discussed above, for each peptide, one or more of the parent-daughter ion pair transitions can be monitored.

Table 1 below shows sequences SEQ ID NOS: 1-4 of the peptides determined, according to the present teachings, to be specific to pork, along with their optimal MRM Q1, Q3 parent-daughter ion transitions along with a fragment identifier of the product ion in brackets. According to various embodiments, these observed peptides and transitions can be used to enable a reliable quantitation of the pork present in the sample.

TABLE 1

| Pork (Sus scrofa) | Q1 | Q3 |
|---|---|---|
| SLYSSAENEPPVPLVR | 453.2 | 581.3 (+2y7) |
| (SEQ ID NO: 1) | 453.2 | 480.3 (+2b9) |
| GGPLTAAYR | 879.5 | 777.5 (+2y5) |
| (SEQ ID NO: 2) | 879.5 | 981.4 (+2y4) |
| SALAHAVQSSR | 563.8 | 784.4 (+2y7) |
| (SEQ ID NO: 3) | 563.8 | 392.7 (+2y7+2) |
| TLAFLFAER | 534.3 | 853.5 (+2y7) |
| (SEQ ID NO: 4) | 534.3 | 782.4 (+2y6) |

According to some embodiments, the method can comprise detecting and/or quantifying beef in the sample by detecting at least one isolated peptide specific to beef, for example, one or more of the peptides having an amino acid sequence of SEQ ID NOS: 5-8 identified herein. For example, LC-MS/MS can be used to determine the presence and/or quantity of beef-specific peptides in the sample. In one exemplary embodiment, a triple quadrupole mass spectrometer can be used to monitor selected Multiple Reaction Monitoring (MRM) transitions. In some embodiments, the beef-specific peptide can have the amino acid sequence of SEQ ID NO: 5 identified herein, and the method can include monitoring at least one parent-daughter ion pair transition having an m/z value of about 462/722 or 462/575. In other embodiments, the beef-specific peptide can have the amino acid sequence of SEQ ID NO: 6 identified herein, and the method can include monitoring at least one parent-daughter ion pair transition having an m/z value of about 582/951 or 582/708. In other embodiments, the beef-specific peptide can have the amino acid sequence of SEQ ID NO: 7 identified herein, and the method can include monitoring at least one parent-daughter ion pair transition having an m/z value of about 595/974 or 595/215. In other embodiments, the beef-specific peptide can have the amino acid sequence of SEQ ID NO: 8, and the method can include monitoring at least one parent-daughter ion pair transition having an m/z value of about 583/703 or 583/759.

In one exemplary embodiment, the method can include monitoring multiple parent-daughter ion pair transitions associated with each beef-specific peptide. By way of example, the beef-specific peptide having the amino acid sequence of SEQ ID NO: 5 can be identified by monitoring one or both of the parent-daughter ion pair transitions having an m/z value of about 462/722 or 462/575.

In one embodiment, the method for detecting or quantifying beef in the sample can include detecting multiple beef-specific peptides. By way of non-limiting example, beef can be detected and/or quantified by using any combination, or all, of the peptides having the amino acid sequences of SEQ ID NOS: 5-8 identified herein. As discussed above, for each peptide, one or more of the parent-daughter ion pair transitions can be monitored.

Table 2 below shows sequences SEQ ID NOS: 5-8 of the peptides determined, according to the present teachings, to be specific to beef, along with their optimal MRM Q1, Q3 parent-daughter ion transitions along with a fragment identifier of the product ion in brackets. According to various embodiments, these observed peptides and transitions can be used to enable a reliable quantitation of the beef present in the sample.

TABLE 2

| Beef (Bos taurus) | Q1 | Q3 |
|---|---|---|
| LVNELTEFAK (SEQ ID NO: 5) | 461.7 461.7 | 722.4 (+2y8) 575.3 (+2y6) |
| AEFVEVTK (SEQ ID NO: 6) | 582.3 582.3 | 951.5 (+2y6) 708.4 (+2y5) |
| TLEDQVNELK (SEQ ID NO: 7) | 594.8 594.8 | 974.5 (+2y8) 215.1 (+2b2) |
| VELPSLIPVILEKPAK (SEQ ID NO: 8) | 582.7 582.7 | 702.9 (+3y9) 759.5 (+3y14) |

According to some embodiments, the method can comprise detecting and/or quantifying lamb in the sample by detecting at least one isolated peptide specific to lamb, for example, one or more of the peptides having an amino acid sequence of SEQ ID NOS: 9-12 identified herein. For example, LC-MS/MS can be used to determine the presence and/or quantity of lamb-specific peptides in the sample. In one exemplary embodiment, a triple quadrupole mass spectrometer can be used to monitor selected Multiple Reaction Monitoring (MRM) transitions. In some embodiments, the lamb-specific peptide can have the amino acid sequence of SEQ ID NO: 9 identified herein, and the method can include monitoring at least one parent-daughter ion pair transition having an m/z value of about 718/1037 or 718/745. In other embodiments, the lamb-specific peptide can have the amino acid sequence of SEQ ID NO: 10 identified herein, and the method can include monitoring at least one parent-daughter ion pair transition having an m/z value of about 623/523 or 623/823. In other embodiments, the lamb-specific peptide can have the amino acid sequence of SEQ ID NO: 11 identified herein, and the method can include monitoring at least one parent-daughter ion pair transition having an m/z value of about 515/659 or 515/832. In other embodiments, the lamb-specific peptide can have the amino acid sequence of SEQ ID NO: 12, and the method can include monitoring at least one parent-daughter ion pair transition having an m/z value of about 431/589 or 431/862.

In one exemplary embodiment, the method can include monitoring multiple parent-daughter ion pair transitions associated with each lamb-specific peptide. By way of example, the lamb-specific peptide having the amino acid sequence of SEQ ID NO: 9 can be identified by monitoring one or both of the parent-daughter ion pair transitions having an m/z value of about 718/1037 or 718/745.

In one embodiment, the method for detecting or quantifying lamb in the sample can include detecting multiple lamb-specific peptides. By way of non-limiting example, lamb can be detected and/or quantified by using any combination, or all, of the peptides having the amino acid sequences of SEQ ID NOS: 9-12 identified herein. As discussed above, for each peptide, one or more of the parent-daughter ion pair transitions can be monitored.

Table 3 below shows sequences SEQ ID NOS: 9-12 of the peptides determined, according to the present teachings, to be specific to lamb, along with their optimal MRM Q1, Q3 parent-daughter ion transitions along with a fragment identifier of the product ion in brackets. According to various embodiments, these observed peptides and transitions can be used to enable a reliable quantitation of the lamb present in the sample.

TABLE 3

| Lamb (Ovis aries) | Q1 | Q3 |
|---|---|---|
| VGGNAGAYGAEALER (SEQ ID NO: 9) | 717.9 717.9 | 1036.5 (+2y10) 745.4 (+2y7) |
| HHGNEFTPVLQADFQK (SEQ ID NO: 10) | 623.3 623.3 | 523.3 (+3y9+2) 823.3 (+3b7) |
| LLGSLDIDHNQYR (SEQ ID NO: 11) | 515.3 515.3 | 659.3 (+3y11+2) 832.4 (+3y6) |
| LTGGVMHYGNLK (SEQ ID NO: 12) | 430.6 430.6 | 588.8 (+3y11+2) 862.4 (+3y7) |

According to some embodiments, the method can comprise detecting and/or quantifying chicken in the sample by detecting at least one isolated peptide specific to chicken, for example, one or more of the peptides having an amino acid sequence of SEQ ID NOS: 13-16 identified herein. For example, LC-MS/MS can be used to determine the presence and/or quantity of chicken-specific peptides in the sample. In one exemplary embodiment, a triple quadrupole mass spectrometer can be used to monitor selected Multiple Reaction Monitoring (MRM) transitions. In some embodiments, the chicken-specific peptide can have the amino acid sequence of SEQ ID NO: 13 identified herein, and the method can include monitoring at least one parent-daughter ion pair transition having an m/z value of about 482/213 or 482/750. In other embodiments, the chicken-specific peptide can have the amino acid sequence of SEQ ID NO: 14 identified herein, and the method can include monitoring at least one parent-daughter ion pair transition having an m/z value of about 768/923 or 768/1037. In other embodiments, the chicken-specific peptide can have the amino acid sequence of SEQ ID NO: 15 identified herein, and the method can include monitoring at least one parent-daughter ion pair transition having an m/z value of about 789/890 or 789/213. In other embodiments, the chicken-specific peptide can have the amino acid sequence of SEQ ID NO: 16, and the method can include monitoring at least one parent-daughter ion pair transition having an m/z value of about 684/1136 or 684/1006.

In one exemplary embodiment, the method can include monitoring multiple parent-daughter ion pair transitions associated with each chicken-specific peptide. By way of example, the chicken-specific peptide having the amino acid sequence of SEQ ID NO: 13 can be identified by monitoring one or both of the parent-daughter ion pair transitions having an m/z value of about 482/213 or 482/750.

In one embodiment, the method for detecting or quantifying chicken in the sample can include detecting multiple chicken-specific peptides. By way of non-limiting example, chicken can be detected and/or quantified by using any combination, or all, of the peptides having the amino acid sequences of SEQ ID NOS: 13-16 identified herein. As discussed above, for each peptide, one or more of the parent-daughter ion pair transitions can be monitored.

Table 4 below shows sequences SEQ ID NOS: 13-16 of the peptides determined, according to the present teachings, to be specific to chicken, along with their optimal MRM Q1, Q3 parent-daughter ion transitions along with a fragment identifier of the product ion in brackets. According to various embodiments, these observed peptides and transitions can be used to enable a reliable quantitation of the chicken present in the sample.

TABLE 4

| Chicken (Gallus gallus) | Q1 | Q3 |
|---|---|---|
| LSVEALNSLEGEFK (SEQ ID NO: 13) | 481.8 481.8 | 213.2 (+2y8) 750.4 (+2y9) |
| VLTPELYK (SEQ ID NO: 14) | 768.4 768.4 | 923.4 (+2b2) 1036.5 (+2y6) |
| MTEEEVEELMK (SEQ ID NO: 15) | 789.4 789.4 | 890.5 (+2y9) 213.2 (+2y8) |
| IVESMQSTLDAEVR (SEQ ID NO: 16) | 684.3 684.3 | 1135.5 (+2b2) 1006.5 (+2y8) |

According to some embodiments, the method can comprise detecting and/or quantifying duck in the sample by detecting at least one isolated peptide specific to duck, for example, one or more of the peptides having an amino acid sequence of SEQ ID NOS: 17-20 identified herein. For example, LC-MS/MS can be used to determine the presence and/or quantity of duck-specific peptides in the sample. In one exemplary embodiment, a triple quadrupole mass spectrometer can be used to monitor selected Multiple Reaction Monitoring (MRM) transitions. In some embodiments, the duck-specific peptide can have the amino acid sequence of SEQ ID NO: 17 identified herein, and the method can include monitoring at least one parent-daughter ion pair transition having an m/z value of about 677/1122 or 677/992. In other embodiments, the duck-specific peptide can have the amino acid sequence of SEQ ID NO: 18 identified herein, and the method can include monitoring at least one parent-daughter ion pair transition having an m/z value of about 977/946 or 977/1442. In other embodiments, the duck-specific peptide can have the amino acid sequence of SEQ ID NO: 19 identified herein, and the method can include monitoring at least one parent-daughter ion pair transition having an m/z value of about 550/820 or 550/473. In other embodiments, the duck-specific peptide can have the amino acid sequence of SEQ ID NO: 20, and the method can include monitoring at least one parent-daughter ion pair transition having an m/z value of about 693/954 or 693/826.

In one exemplary embodiment, the method can include monitoring multiple parent-daughter ion pair transitions associated with each duck-specific peptide. By way of example, the duck-specific peptide having the amino acid sequence of SEQ ID NO: 17 can be identified by monitoring one or both of the parent-daughter ion pair transitions having an m/z value of about 677/1122 or 677/992.

In one embodiment, the method for detecting or quantifying duck in the sample can include detecting multiple duck-specific peptides. By way of non-limiting example, duck can be detected and/or quantified by using any combination, or all, of the peptides having the amino acid sequences of SEQ ID NOS: 17-20 identified herein. As discussed above, for each peptide, one or more of the parent-daughter ion pair transitions can be monitored.

Table 5 below shows sequences SEQ ID NOS: 17-20 of the peptides determined, according to the present teachings, to be specific to duck, along with their optimal MRM Q1, Q3 parent-daughter ion transitions along with a fragment identifier of the product ion in brackets. According to various embodiments, these observed peptides and transitions can be used to enable a reliable quantitation of the duck present in the sample.

TABLE 5

| Duck (Anas peking) | Q1 | Q3 |
|---|---|---|
| MTEEEVDELMK (SEQ ID NO: 17) | 677.3 677.3 | 1121.5 (+2y9) 992.5 (+2y8) |
| TLALLFANYGGADAEAGGGGK (SEQ ID NO: 18) | 977.0 977.0 | 946.4 (+2y12) 1441.6 (+2y16) |
| VAAALVEAVNHIDDIAGALSK (SEQ ID NO: 19) | 549.8 549.8 | 820.5 (+3y16+2) 473.3 (+3y19+2) |
| MFLAYPQTK (SEQ ID NO: 20) | 693.0 693.0 | 954.0 (+2y4) 826.4 (+2y7) |

According to some embodiments, the method can comprise detecting and/or quantifying horse in the sample by detecting at least one isolated peptide specific to horse, for example, one or more of the peptides having an amino acid sequence of SEQ ID NOS: 21-24 identified herein. For example, LC-MS/MS can be used to determine the presence and/or quantity of horse-specific peptides in the sample. In one exemplary embodiment, a triple quadrupole mass spectrometer can be used to monitor selected Multiple Reaction Monitoring (MRM) transitions. In some embodiments, the horse-specific peptide can have the amino acid sequence of SEQ ID NO: 21 identified herein, and the method can include monitoring at least one parent-daughter ion pair transition having an m/z value of about 508/803 or 508/902. In other embodiments, the horse-specific peptide can have the amino acid sequence of SEQ ID NO: 22 identified herein, and the method can include monitoring at least one parent-daughter ion pair transition having an m/z value of about 888/1030 or 888/973. In other embodiments, the horse-specific peptide can have the amino acid sequence of SEQ ID NO: 23 identified herein, and the method can include monitoring at least one parent-daughter ion pair transition having an m/z value of about 818/948 or 818/847. In other embodiments, the duck-specific peptide can have the amino acid sequence of SEQ ID NO: 24, and the method can include monitoring at least one parent-daughter ion pair transition having an m/z value of about 583/646 or 583/759.

In one exemplary embodiment, the method can include monitoring multiple parent-daughter ion pair transitions associated with each horse-specific peptide. By way of example, the horse-specific peptide having the amino acid sequence of SEQ ID NO: 21 can be identified by monitoring one or both of the parent-daughter ion pair transitions having an m/z value of about 508/803 or 508/902.

In one embodiment, the method for detecting or quantifying horse in the sample can include detecting multiple horse-specific peptides. By way of non-limiting example, horse can be detected and/or quantified by using any combination, or all, of the peptides having the amino acid sequences of SEQ ID NOS: 21-24 identified herein. As discussed above, for each peptide, one or more of the parent-daughter ion pair transitions can be monitored.

Table 6 below shows sequences SEQ ID NOS: 21-24 of the peptides determined, according to the present teachings, to be specific to horse, along with their optimal MRM Q1, Q3 parent-daughter ion transitions along with a fragment identifier of the product ion in brackets. According to various embodiments, these observed peptides and transitions can be used to enable a reliable quantitation of the horse present in the sample.

TABLE 6

| Horse (Equus ferus) | Q1 | Q3 |
|---|---|---|
| LVNDLTGQR (SEQ ID NO: 21) | 508.3 | 803.4 (+2y7) |
|  | 508.3 | 902.5 (+2y8) |
| TLALLFSGPASADAEAGGK (SEQ ID NO: 22) | 888.5 | 1030.5 (+2y12) |
|  | 888.5 | 973.5 (+2y11) |
| VVETMQTMLDAEIR (SEQ ID NO: 23) | 818.4 | 948.5 (+2y8) |
|  | 818.4 | 847.4 (+2y7) |
| EFEIGNLQSK (SEQ ID NO: 24) | 582.8 | 646.4 (+2y6) |
|  | 582.8 | 759.4 (+2y7) |

While the above described embodiments exemplify the use of a triple quadrupole tandem mass spectrometer, it should be appreciated that included within the scope of the present teachings is the usage of other tandem mass spectrometer type systems which can include, but is not limited to Quadrupole-Time of Flight (TOF), Quadrupole-Trap, and TOF-TOF systems.

In some embodiments, two or more of the above animal species can be detected and/or quantified by detecting, via LC-MS/MS, one or more peptides specific for each type of meat, such as those discussed above, where for each peptide one or both of the MRM transitions, such as those discussed above, can be monitored. In one embodiment, for example, pork proteins can be detected in a sample by monitoring both of the MRM transitions for one of the peptides specific to pork (e.g., monitoring the MRM transitions of 453/581 and 453/480 for the peptide having the amino acid sequence of SEQ. ID NO. 1 and monitoring the MRM transitions 879/777 and 879/981 for the peptide having the amino acid sequence of SEQ. ID NO. 2) and one peptide specific to beef (e.g., monitoring the MRM transitions of 462/722 and 462/575 for the peptide having the amino acid sequence of SEQ. ID NO. 5). In some embodiments, all of the animal meat species are detected and monitored using one or more of the peptides and one or more of each of the transitions for each of the one or more peptides described herein.

In some embodiments, the contamination of a meat sample by one or more of pork, beef, lamb, chicken, duck and/or horse can be determined by monitoring for the one or more peptides described above using the one or more of each of the transitions for each of the one or more peptides. For example, in one embodiment, a sample of beef may be contaminated by one or more of pork, lamb, chicken, duck and/or horse and that by monitoring for peptides specific to pork, lamb, chicken, duck and/or horse meat utilizing one or more of the peptides and/or transitions referred to in the within teachings, the determination of a contamination may be made. In other embodiments, a sample of lamb may be checked for contamination by pork, beef, chicken, duck and/or horse using the within teachings. As should be appreciated, the detection of contamination of a specific type of meat by meat of another type can be performed by detecting the presence of one or more of the peptides and the one or more of each of the transitions for each of the one or more peptides described herein.

According to some embodiments, a kit for use in the mass spectrometric testing of a sample for at least one of pork, beef, lamb, chicken, duck and/or horse is provided. The kit can include one or more isolated peptides specific to pork, beef, lamb, chicken, duck and/or horse. For example, the kit can include one or more isolated pork-specific peptides having the amino acid sequence of SEQ ID NO: 1, SEQ ID NO: 2, SEQ ID NO: 3 or SEQ ID NO: 4. In one aspect, the kit can include one or more isolated beef-specific peptides having the amino acid sequence of SEQ ID NO: 5, SEQ ID NO: 6, SEQ ID NO: 7, or SEQ ID NO: 8. In one embodiment, the kit can include one or more isolated lamb-specific peptides, such as those peptides having the amino acid sequence of SEQ ID NO: 9, SEQ ID NO: 10, SEQ ID NO: 11 or SEQ ID NO: 12. Alternatively or in addition, the kit can include one or more isolated peptides specific to the chicken, such as those peptides having the amino acid sequence of SEQ ID NO: 13, SEQ ID NO: 14, SEQ ID NO: 15 or SEQ ID NO: 16. In one embodiment, the kit can include one or more duck-specific peptides having the amino acid sequence of SEQ ID NO: 17, SEQ ID NO: 18, SEQ ID NO: 19, SEQ ID NO: 20. The kit can also include one or more horse-specific peptides having the amino acid sequence of SEQ ID NO: 21, SEQ ID NO: 22, SEQ ID NO: 23 or SEQ ID NO: 24. In some embodiments, the kit can comprise at least one isolated peptide specific to each of pork, beef, lamb, chicken, duck and/or horse. For example, the kit can comprise one of each of the isolated peptides corresponding to SEQ ID NOS: 1-24 identified herein. Alternatively, the kit can comprise one peptide selected from the group corresponding to SEQ ID NOS. 1-4, one peptide selected from the group corresponding to SEQ ID NOS. 5-8, one peptide selected from the group corresponding to SEQ ID NOS. 9-12, one peptide selected from the group corresponding to SEQ ID NOS. 13-16, and one peptide selected from the group corresponding to SEQ ID NOS. 17-20. In addition, the kit may comprise one peptide selected from the group corresponding to SEQ ID NOS. 21-24. In some embodiments, the peptides can be isotopically labeled (e.g., using 15N, 13C)

According to some embodiments, a kit for use in the mass spectrometric testing of a sample for at least one of pork, beef, lamb, chicken, duck and/or horse is provided. The kit can include, for example, at least one proteolytic enzyme for fragmenting one or more of pork, beef, lamb, chicken, duck and/or horse into a plurality of peptides. For example, the proteolytic enzyme can be effective to fragment the meat samples into a plurality of peptides, at least one of which has the amino acid sequence of SEQ ID NOS. 1-24. The kit can also include at least one reagent for quantifying at least one of the plurality of peptides having an amino acid sequence of SEQ ID NO: 1-24 using a mass spectrometer.

Various processes and reagents can be effective to prepare the sample for mass spectrometric analysis and/or fragment the meat samples into a plurality of peptides. For example, in one exemplary embodiment, the proteolytic enzyme can be trypsin that can lyse the meat samples into a plurality of peptides. In some embodiments, the kit can include an LC column on which a proteolytic enzyme, such as trypsin, is immobilized. The kit can also comprise digestion components, including buffers enzymes, alkylating agents, reducing agents, and optionally, other reagents and/or components. In some embodiments, the kit can comprise, for example, a homogeneous assay such that the user need only add a sample.

In some embodiments, the kit can comprise calibration or normalization reagents or standards. For example, the kit can comprise at least one peptide specific to each of pork, beef, lamb, chicken, duck and/or horse for calibrating the quantitation of the animal-specific peptides. By way of non-limiting example, the kit can contain solutions for each of the animal-specific peptides at known concentrations such that a calibration curve can be constructed. In some embodiments, the kit can contain peptides of at least one of the animals of interest (e.g., pork, beef, lamb, chicken, duck and/or horse) for calibrating the quantitation of the animal-specific peptides or the meat(s) themselves. For example, the kit can include a known amount of each of pork, beef, lamb, chicken, duck and/or horse. Alternatively or in addition, calibration can be performed by spiking the sample with at least one isotopically-enriched peptide having the same amino acid sequence as that of a peptide of interest. Accordingly, the kit can include one or more isotopically-enriched peptides corresponding to each of SEQ ID NOS. 1-24.

According to some embodiments, different transitions can be used to measure and benchmark assay results, depending on various factors. Accordingly, the kit can comprise different transition values and/or suggested settings, useful for enabling comparative measurements between a sample and one or more control reagents. The kit can include information relating to Q1 and Q3 transition values for each of the animal-specific peptides. For example, in one embodiment, the kit can comprise each of the isolated peptides of SEQ ID NOS: 1-24 identified herein, and further can comprise instructions for quantifying the at least one of the peptides using a mass spectrometer. Information pertaining to instrument settings that can or should be used to perform an assay can also be included in the kit. Information pertaining to sample preparation, operating conditions, volumetric amounts, temperature settings, and the like, can be included with the kit.

According to some embodiments, different transitions can be used to measure and benchmark assay results, depending on various factors. Accordingly, the kit can comprise different transition values and/or suggested settings, useful to make comparative measurements between a sample and one or more control reagents. The kit can include instructions to measure specific pairs of transition values, for example, the Q1/Q3 transition pair, or the values of one or more different transition pairs.

The kit can be packaged in a hermetically sealed container containing one or more reagent vessels and appropriate instructions. An electronic medium can also be contained within the kit and can store and/or provide electronic information pertaining to one or more assays, measurement values, transition pairs, operating instructions, software for carrying out operations, a combination thereof, or the like.

According to some aspects, software is provided which can control the processes and/or perform the calculations described herein. For example, the software can provide instructions to a mass spectrometer to monitor one or more specific precursor-product ion pair transitions.

The software can include modules for generating calibration data, e.g., based on mass spectrometric analysis of calibrations standards provided with a kit, and modules for receiving and analyzing mass spectrometric data (e.g., LC-MS/MS data) to identify one or more of the above peptides and MRM transitions. Upon identification of one or more peptides specific to one of the above animals, the software can utilize the calibration data to quantify those peptides and the associated meat species.

In several embodiments, a system for detecting pork, beef, lamb, chicken, duck and horse meat may be is described. The system comprises a tandem mass spectrometer configured to perform parent-daughter ion transition monitoring; and a processor in communication with the tandem mass spectrometer that sends instructions to the tandem mass spectrometer to detect the presence of peptides unique to pork, beef, lamb, chicken, duck and horse. The peptides may be any of the peptides SEQ ID NO 1-24 and the detection may be performed by monitoring one or more parent-daughter ion transitions selected from the transitions referred to in Tables 1-6.

EXAMPLES

Figure 17:
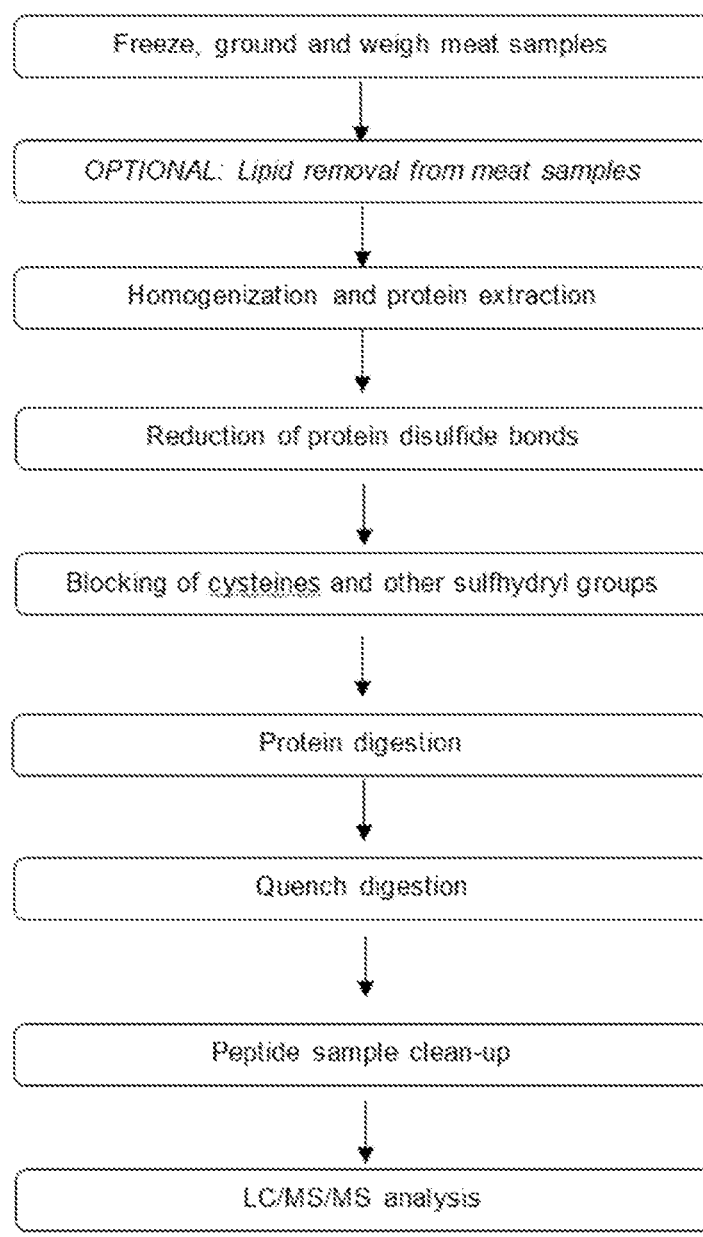
FIG. 17 illustrates one exemplary procedure for preparing samples for analysis according to various embodiments of the present teachings.

The applicants' teachings can be even more fully understood with reference to the examples and resulting data that follow. Other embodiments of the present teachings will be apparent to those skilled in the art from consideration of the present specification and practice of the present teachings disclosed herein. It is intended that these examples be considered as exemplary only. FIG. 17 shows an exemplary flowchart of preparation of meat sample according to some embodiments of the present teachings.

Preparation of Solutions

Extraction Buffer—Tris(2-Amino-2-(hydroxymethyl)-1, 3-propanediol, 0.61 g), Urea (36.04 g) and Thiourea (7.61 g) were dissolved in HPLC-grade water and made up to a volume of 100 mL to make an extraction buffer containing 50 mM Tris, 6M Urea and 1 M thiourea.

Ammonium bicarbonate Buffer—Ammonium bicarbonate (158 g) is made up to a volume of 20 mL with HPLC water to make a 100 mM solution.

Reducing Agent—tris-(2-carboxyethyl)-phosphine (TCEP) (15.02 mg) is made up to a solution of 0.6 mL with 100 mM ammomium bincarbonate buffer to make a solution containing 100 mM TCEP.

Cysteine Blocking Reagent—methyl methane-thio-sulfonate (MMTS) (10 µL, >98%, ~10.6 M) is made up to a solution of 530 µL by adding approximately 520 µL of 100 mM ammonium bicarbonate to make a solution containing 200 mM MMTS.

Trypsin Solution—lyophilized trypsin enzyme powder (1 mg) was added to 1.0 mL of 1 mM HCl solution and vortexed to dissolve the trypsin to make a 1 µg/µL trypsin solution. Aliquot the trypsin solution into 0.6 mL tube with 50 µL per tube.

System Suitability Test Mixture—1 nmol bovine serum albumin (BSA) tryptic digest standard was dissolved in 2 ml 5% acetonitrile, 0.1% formic acid in water to make 0.5 pmol/µL BSA digest stock. 20 µL of BSA digest stock was mixed with 180 µL 5% acetonitrile, 0.1% formic acid in water to create a test sample containing 50 fmol/µL.

Meat Product Preparation Procedures

Test Standard Samples were made according to the compositions contained in Table 7

TABLE 7

| Contaminant | | Pork Homogenate (µL) | Beef Homogenate (µL) | Lamb Homogenate (µL) | Chicken Homogenate (µL) | Duck Homogenate (µL) |
|---|---|---|---|---|---|---|
| Type | Concentration | | | | | |
| Pork | 0% Pork | 0 | 500 | 500 | 500 | 500 |
| | 1% Pork | 20 | 495 | 495 | 495 | 495 |
| Beef | 0% Beef | 500 | 0 | 500 | 500 | 500 |
| | 1% Beef | 495 | 20 | 495 | 495 | 495 |
| Lamb | 0% Lamb | 500 | 500 | 0 | 500 | 500 |
| | 1% Lamb | 495 | 495 | 20 | 495 | 495 |
| Chicken | 0% Chicken | 500 | 500 | 500 | 0 | 500 |
| | 1% Chicken | 495 | 495 | 495 | 20 | 495 |
| Duck | 0% Duck | 500 | 500 | 500 | 500 | 0 |
| | 1% Duck | 495 | 495 | 495 | 495 | 20 |

| Test meat sample | Standard sample | Pork homogenate (µL) | Beef homogenate (µL) | Lamb homogenate (µL) | Chicken or duck homogenate (µL) | Horse homogenate (µL) |
|---|---|---|---|---|---|---|
| Horse | 0% Horse | 500 | 500 | 500 | 500 | 0 |
| | 1% Horse | 495 | 495 | 495 | 495 | 20 |

Weighing Meat Samples 10 g/species of the raw or processed meat product (pork, beef, lamb, chicken, duck and horse) was weighed out avoiding the inclusion of fat as much as possible. The meat was cut into small pieces (smaller than 0.5 cm×0.5 cm×0.5 cm) and the meat frozen in −20° C. or lower for 1 hour. Each frozen meat sample was ground into fine powder or paste ensuring that the meat is well homogenized.

1 g of each ground meat sample (pork, beef, lamb, chicken, duck and unknown samples) was weighed and transferred to individual 15 mL polypropylene centrifuge tube.

If the sample(s) contain a large amount of fat, an optional step of fat removal may be performed which involves adding 5 mL of hexane to each tube and mixing well using a 3D-platform or vortex mixer for 15 min. Centrifuging the samples at 4000×g for 10 min and then discarding 5 mL of the supernatant and then drying the samples under a gentle flow of nitrogen without heating, or placing the samples in a fume hood with the blower on until completely dry.

Homogenization and Protein Extraction of Meat Samples 5 mL of extraction buffer was added to the meat sample in each of the 15 mL centrifuge tubes. A homogenizer probe was inserted into the protein solution and the meat sample was homogenized at ~20,000 rpm for 5 min in an ice bath. The probe homogenizer was cleaned with soapy water and with deionized water after each homogenization to avoid cross contamination To prepare standard samples based on the compositions according to Table 7, the required meat homogenate solution for each of the compositions was measured out and placed in a new 2 mL microcentrifuge tube to form the mixture. The homogenate was then mixed.

To prepare unknown samples, each unknown meat homogenate was directly distributed into 2 mL microcentrifuge tubes. The total volume of meat homogenate for each sample was usually 3~6 mL meaning that in some cases more than one 2 mL microcentrifuge tube for each sample was needed.

Centrifuge the standard samples and aliquoted unknown samples at 14,000×g for 15 min. Transfer the clear supernatants (for each sample) into 2-mL microcentrifuge tubes. Avoid pipetting the top layer of lipid foam and residue at the bottom of the tube when combining the supernatants.

Transfer 0.4 mL of total extracted clear supernatant into a 2 mL microcentrifuge tube. The remaining protein extract can be stored in −20° C. for future use.

Add 1.4 mL 100 mM ammonium bicarbonate to dilute it for 4.5 times and mix well.

Reduction of Protein Disulfide Bonds and Blockage of Cysteines and Other Sulfhydryl Groups 25 µL of reducing reagent was added to each 2 mL microcentrifuge tube and mix welled. The mixture was allowed to incubate at 60° C. for 60 min.

The samples were cooled at room temperature. 25 µL of cysteine-blocking reagent was then added to each sample and mixed well and allowed to incubate for 30 minutes at room temperature.

Protein Digestion

Add 12 µL of trypsin (1 µg/4) to microcentrifuge tube and mix well and then incubate samples at 37° C. overnight for 4 h or overnight (>12 h). The samples are then cooled to room temperature and 20 µL of formic acid is added to each sample to stop the digestion. The mixture is vortexed to mix well.

Peptide Sample Clean-up

To remove high concentrations of salt buffer which may contaminate the mass spectrometer, the sample is centrifuged for 15 min at 14,000×g. The supernatant is collected and solid phase extraction (SPE, 60 mg bedding size) is applied to the digested samples (supernatant).

The detailed SPE procedure is listed below:

Cartridge activation: 1 mL of methanol, (twice)

Cartridge equilibration: 1 mL of water, (twice)

Sample loading: load the supernatant onto the cartridge with a speed of 1~2 droplets per second or lower Wash: 1 mL of 0.1% formic acid in water, (twice)

Allow the column to stand for 3~5 min after completion of the 2nd wash.

Elution: 0.5 mL of 50% acetonitrile, 0.1% formic acid in water; followed by 0.5 mL 70% acetonitrile, 0.1% formic acid in water (with a speed of 1~2 droplets per second). Collect eluent in a 1.7 mL microcentrifuge tube.

Dry the sample with $N_2$ gas dryer or speed vacuum and then reconstitute the sample by adding 200 μL 5% acetonitrile, 0.1% formic acid in water. Vortex vigorously for 1 min.

Transfer 200 μL of each sample into a 3 kDa MWCO filter unit. Centrifuge at 14,000×g for 15 min and collect filtrate. Transfer the filtrate into 250 μL HPLC vial and inject 10 μL of each sample for LC-MS/MS analysis. For standard samples, 3 injections of each sample are required.

Chromatography

Chromatography was performed using a Shimadzu UPLC system coupled to a Phenomenex Kinetex c18 LC column (100 Å, 2.6 μm, 100×4.6 mm). Mobile phase A:0.1% formic acid in water, Mobile Phase B:0.1% formic acid in acetonitrile. Gradient was 2% to 90% over 16.3 minutes. Flow rate of 0.500 mL/min Other HPLC parameters are included in Table 8 below:

TABLE 8

| Initial Settings | Module |
| --- | --- |
| Pump B concentration | 2.0% |
| Pump B Curve | 0 |
| Minimum pressure | 0 psi |
| Maximum pressure | 6000 psi |
| Autosampler | |
| Use autosampler | Yes |
| Rinsing volume | 1000 μL |
| Needle stroke | 52 mm |
| Rinsing speed | 35 μL/sec |
| Sampling speed | 2.0 μL/sec |
| Purge time | 25.0 min |
| Rinse dip time | 5 sec |
| Rinse mode | Before and after aspiration |
| Cooler Enabled | Yes |
| Cooler Temperature | 10° C. |
| Control Vial Needle Stroke | 52 mm |
| Oven | |
| Enable Oven | Yes |
| Oven Temperature | 40° C. |

Mass Spectrometry

Samples were analyzed on a SCIEX QTRAP® 4500 LC/MS/MS system equipped with a TurbolonSpray® source in positive electrospray ionization mode.

Results

FIG. 1 is a depiction of the complicated nature of pure samples of meat in the LC time scale. Each dot present represents a mass spectrum that was generated for a peptide precursor at a time point given.

Figure 2A:
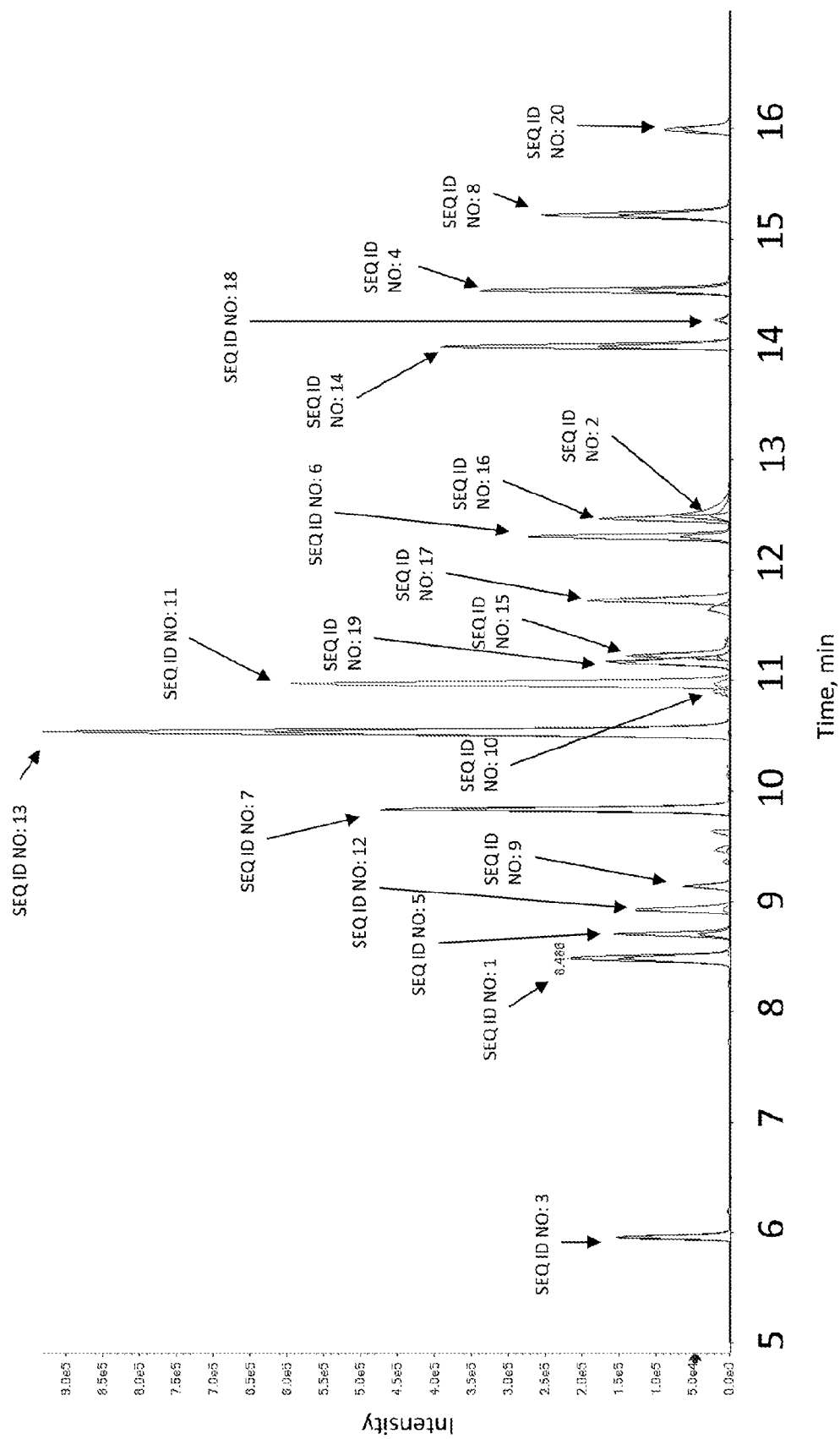
FIG. 2A shows the extracted Ion Chromatogram (XIC) of a protein digestion mixture of 5 types of meat in one embodiment of the present teachings.
Figure 2B:
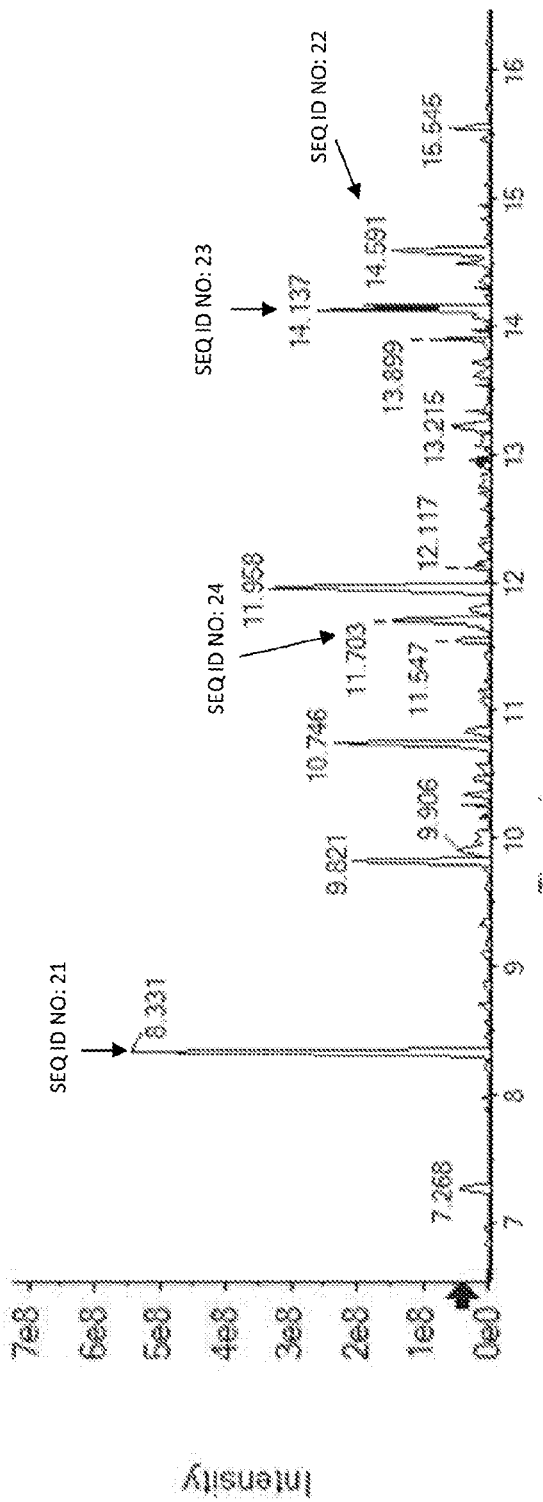
FIG. 2B shows an extracted XIC of a horse meat sample in one embodiment of the present teachings.

FIG. 2A depicts the extracted Ion Chromatogram (XIC) of a protein digestion mixture of 5 types of meat (pork, beef, lamb, chicken and duck) using the teachings described herein.

Figure 3:
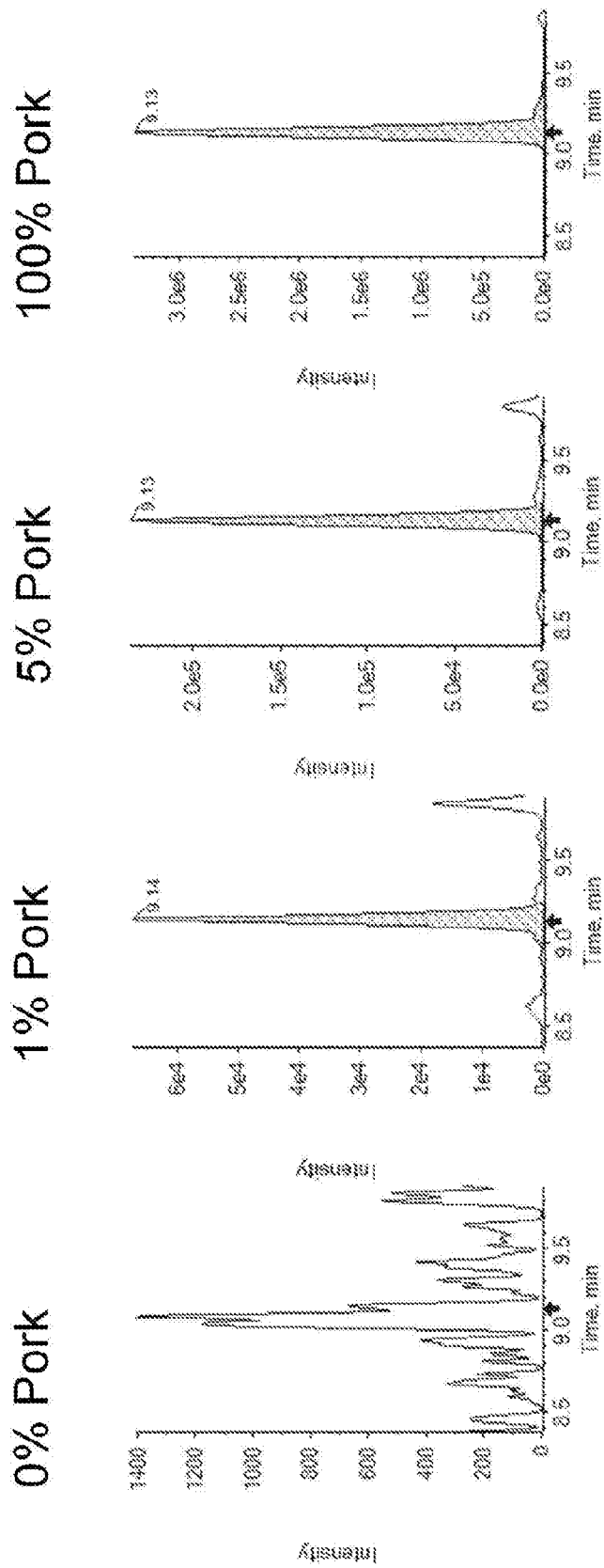
FIG. 3 shows the extracted ion chromatograms for pork at various concentration levels according to various embodiments of the present teachings.

FIG. 3 shows the extracted ion chromatograms for pork at various concentration levels for the peptide having SEQ ID NO: 1 using a parent-daughter ion transition of about 453/581 in a meat mixture containing equal amounts of beef, lamb, chicken and duck obtained according to various embodiments of the present teachings.

Figure 4:
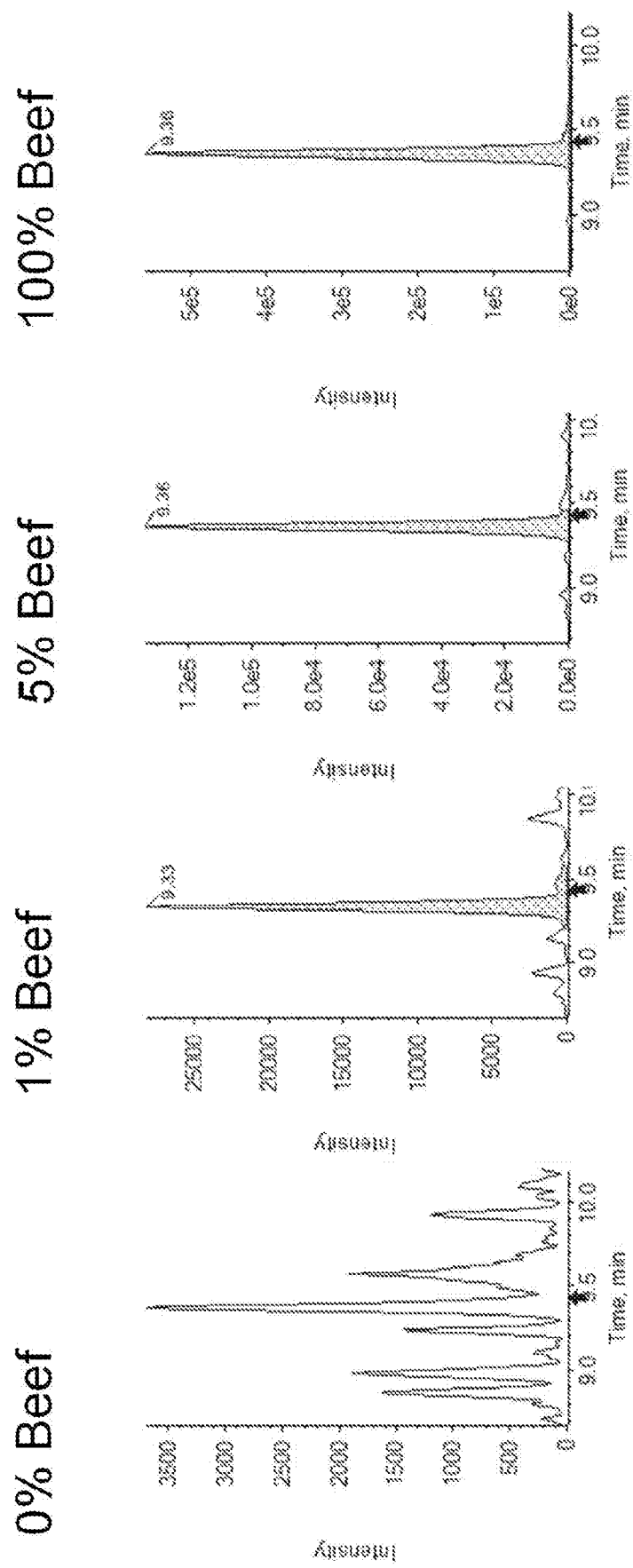
FIG. 4 shows the extracted ion chromatograms for beef at various concentration levels according to various embodiments of the present teachings.

FIG. 4 shows the extracted ion chromatograms for beef at various concentration levels for the peptide having SEQ ID NO: 5 using a parent-daughter ion transition of about 462/722 in a meat mixture containing equal amounts of pork, lamb, chicken and duck obtained according to various embodiments of the present teachings.

Figure 5:
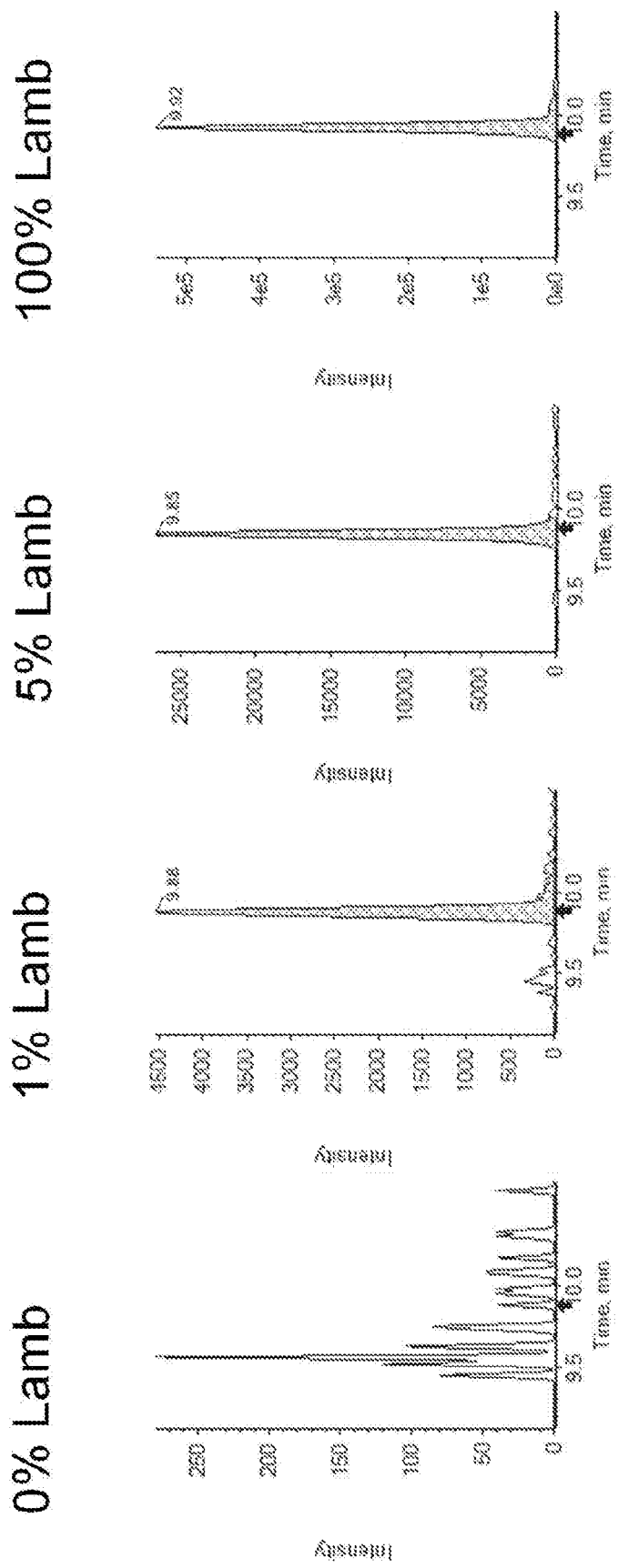
FIG. 5 shows the extracted ion chromatograms for lamb at various concentration levels according to various embodiments of the present teachings.

FIG. 5 shows the extracted ion chromatograms for lamb at various concentration levels for the peptide having SEQ ID NO: 9 using a parent-daughter ion transition of about 718/1037 in a meat mixture containing equal amounts of pork, beef, chicken and duck obtained according to various embodiments of the present teachings.

Figure 6:
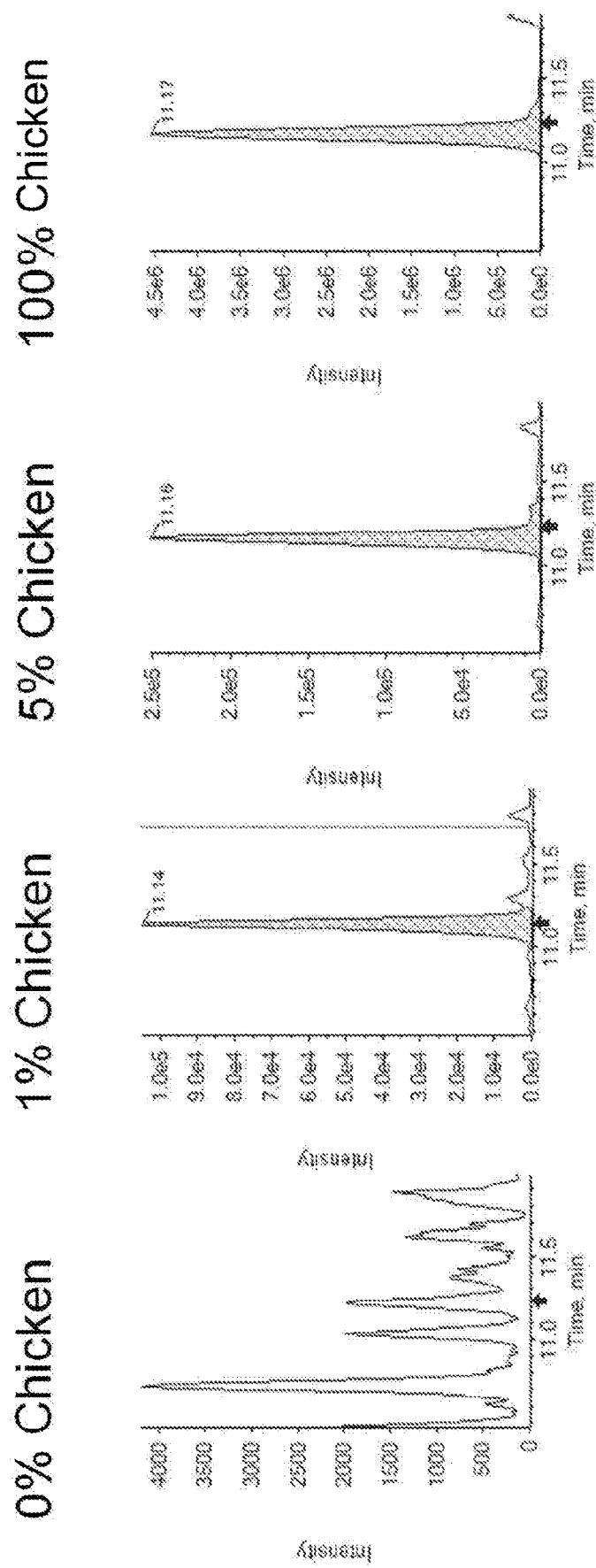
FIG. 6 shows the extracted ion chromatograms for chicken at various concentration levels according to various embodiments of the present teachings.

FIG. 6 shows the extracted ion chromatograms for chicken at various concentration levels for the peptide having SEQ ID NO: 13 using parent-daughter ion transitions of about 482/213 in a meat mixture containing equal amounts of pork, beef, lamb and duck obtained according to various embodiments of the present teachings.

Figure 7:
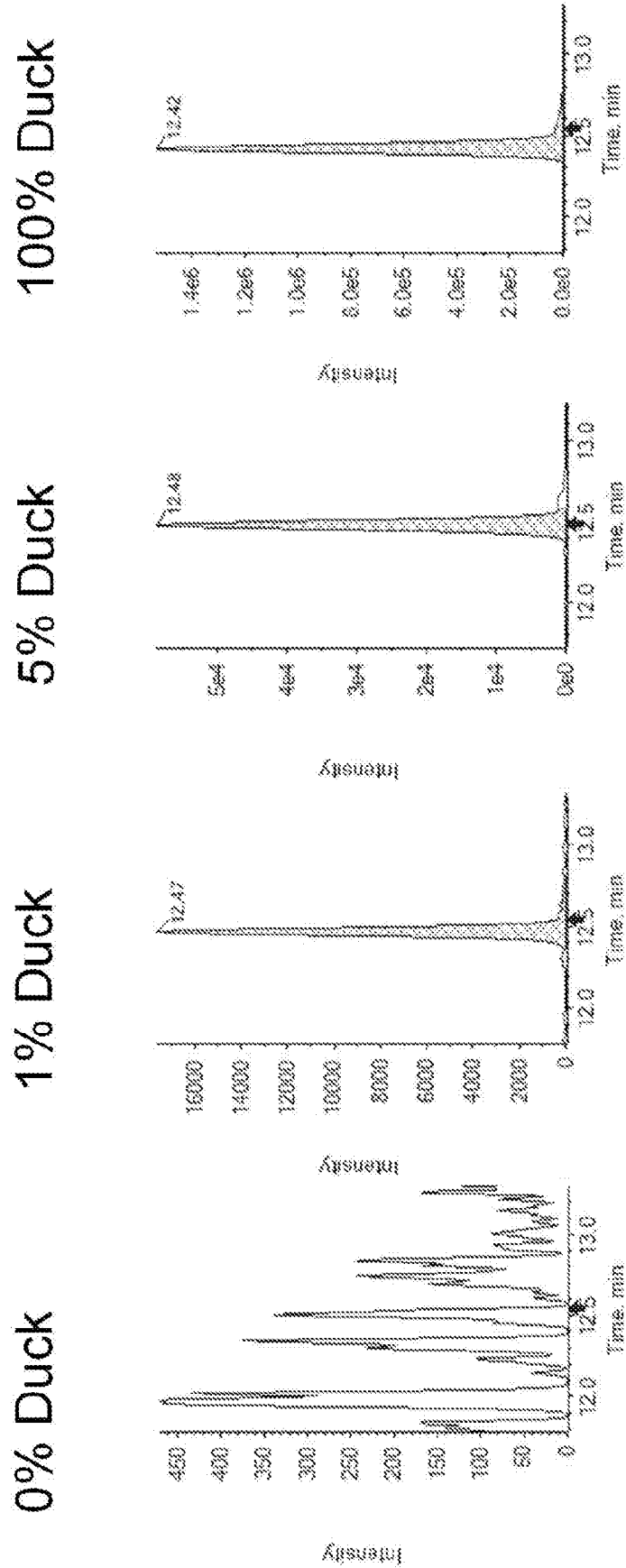
FIG. 7 shows the extracted ion chromatograms for duck at various concentration levels according to various embodiments of the present teachings.

FIG. 7 shows the extracted ion chromatograms for duck at various concentration levels for the peptide having SEQ ID NO: 17 using parent-daughter ion transitions of about 677/1122 in a meat mixture containing equal amounts of pork, beef, lamb and chicken obtained according to various embodiments of the present teachings.

Figure 8:
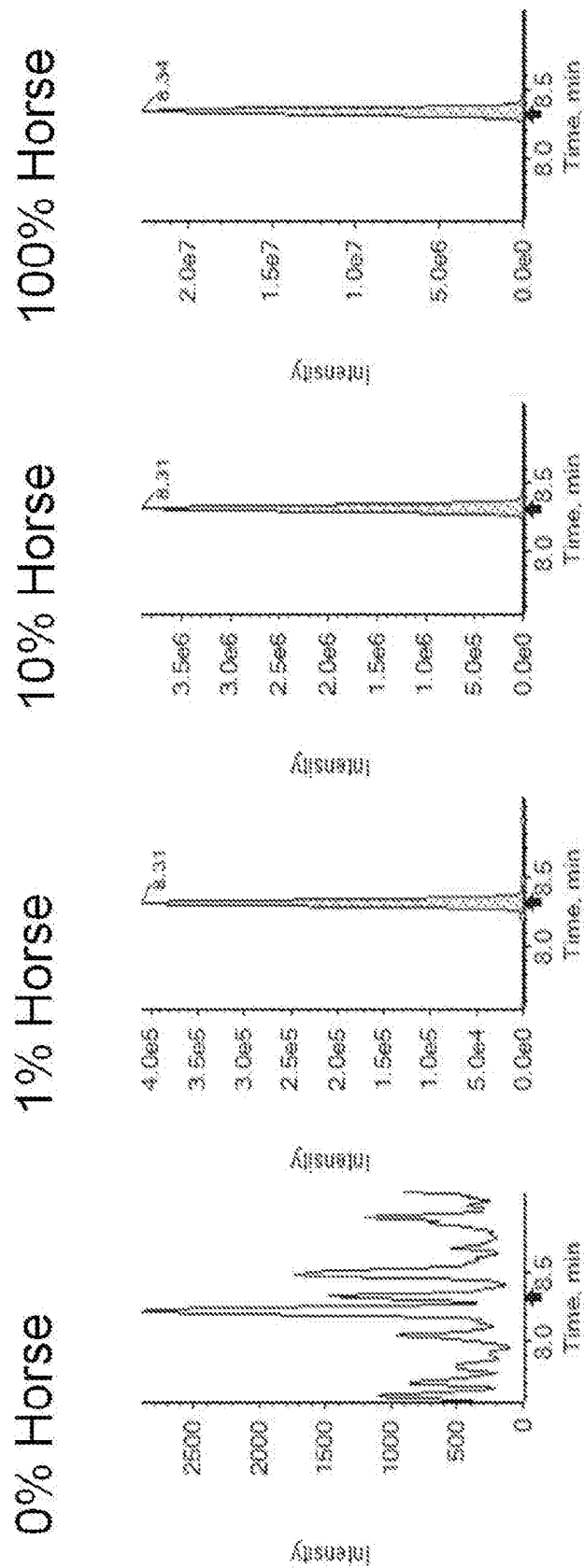
FIG. 8 shows the extracted ion chromatograms for horse at various concentration levels according to various embodiments of the present teachings.
Figure 9:
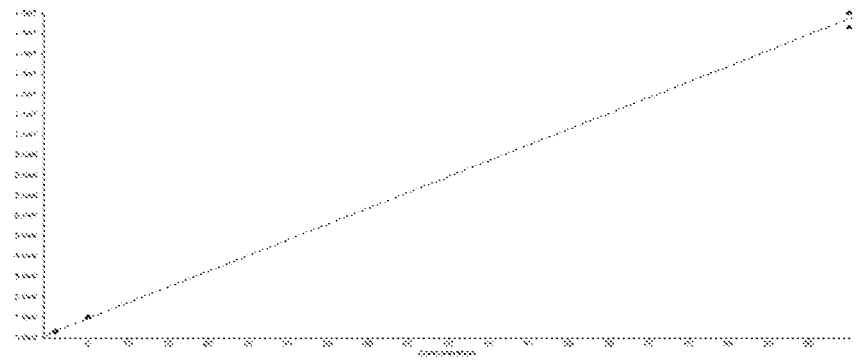
FIGS. 9 to 14 show calibration curves generated from each of pork, beef, lamb, chicken, duck and horse, respectively according to various embodiments of the present teachings.
Figure 10:
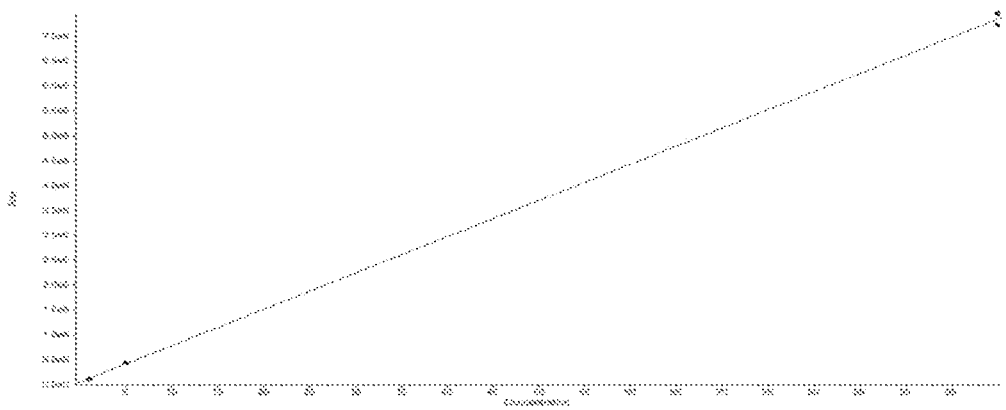
Figure 11:
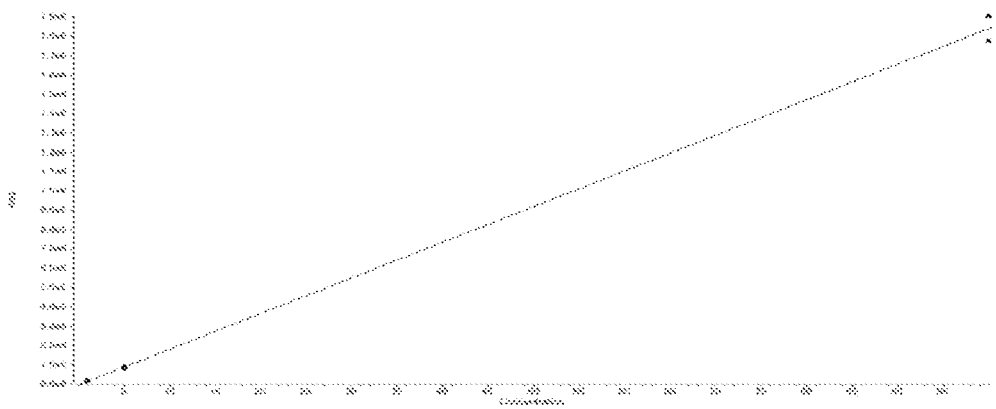
Figure 12:
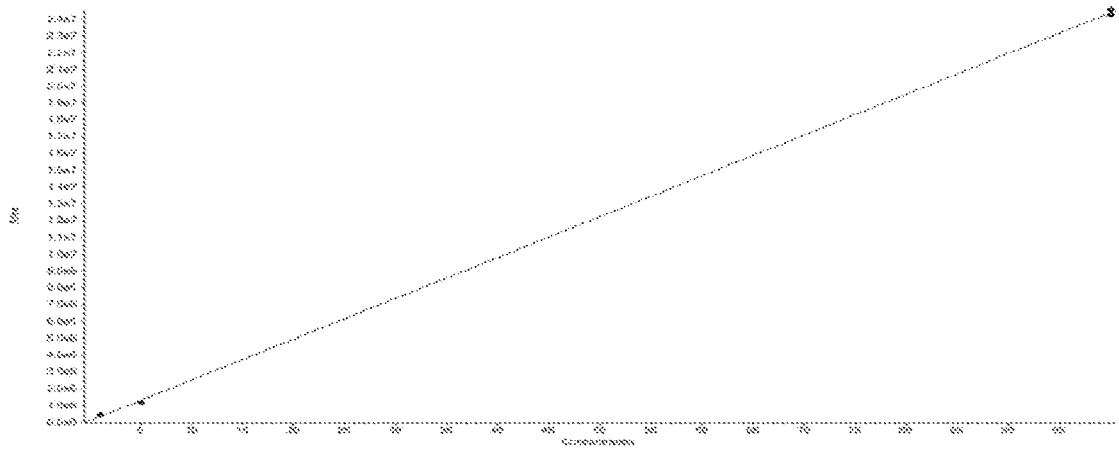
Figure 13:
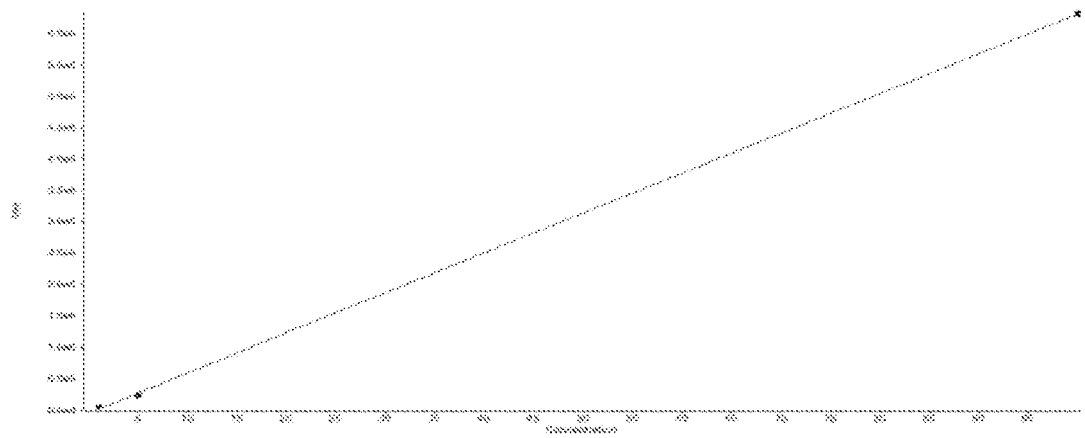
Figure 14:
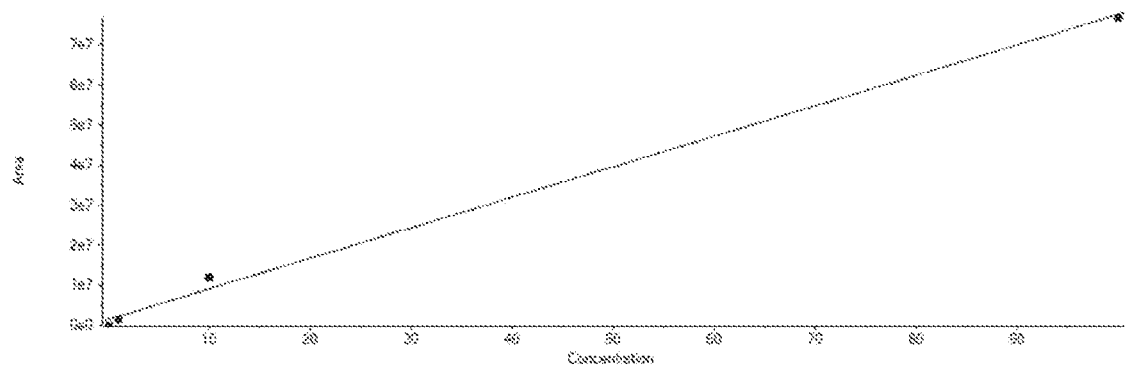

FIG. 8 shows the extracted ion chromatograms for horse at various concentration levels for the peptide having SEQ ID NO: 21 using parent-daughter ion transitions of about 508/902 in a meat mixture containing equal amounts of pork, beef, lamb and chicken obtained according to various embodiments of the present teachings.

FIGS. 9-14 show calibration curves generated from each of pork, beef, lamb, chicken, duck and horse, respectively, obtained from the chromatograms depicted in FIGS. 3 through 8 showing that the peak areas obtained scale with concentration indicating that the within described teachings may be utilized in a quantitative manner to detect meat contamination.

Example 2

Figure 15:
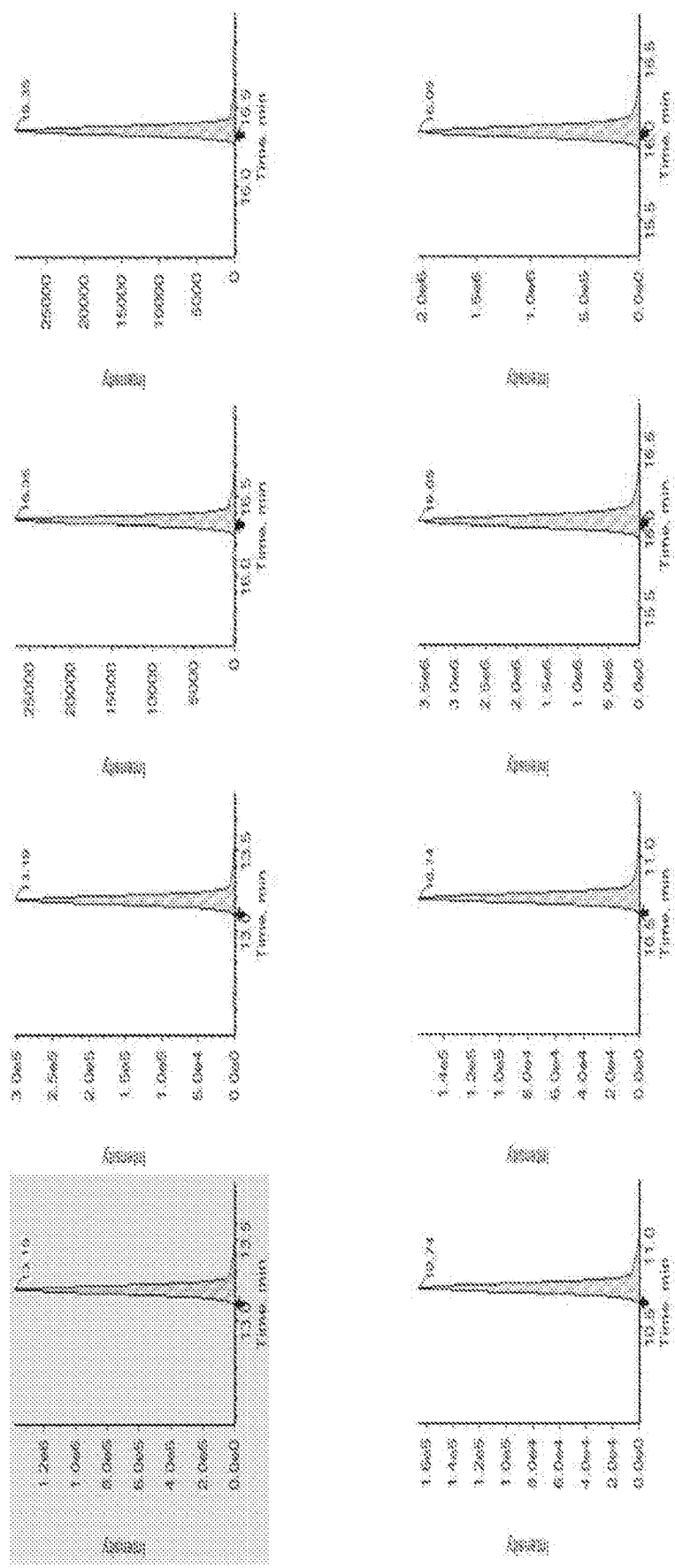
FIG. 15 shows the extracted ion chromatograms for beef in a fast food sample according to various embodiments of the present teachings.

The meat from a cooked hamburger obtained from a fast food restaurant was purchased and analyzed according to the within teachings. FIG. 15 depicts the extracted ion chromatograms for beef utilizing peptides having SEQ ID NO: 5 (two in upper left), SEQ ID NO: 6 (two in upper right), SEQ ID NO: 7 (two in lower left) and SEQ ID NO: 8 (two in lower right) confirming the presence of beef.

Figure 16:
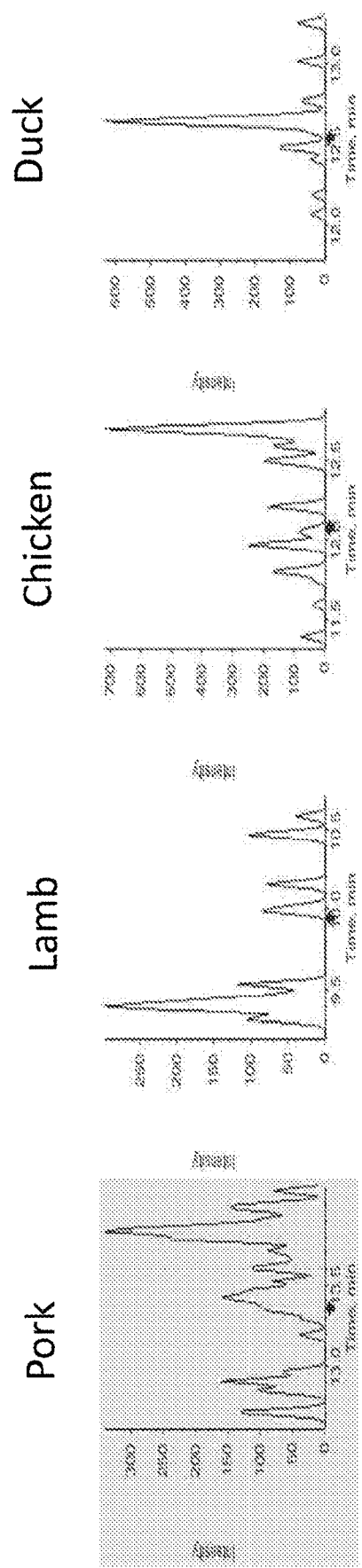
FIG. 16 shows the extracted ion chromatograms for pork, lamb, chicken and duck in a fast food sample according to various embodiments of the present teachings.

FIG. 16 depicts the extracted ion chromatograms for pork, lamb, chicken and duck, indicating that in comparison to background, no contamination of other meats was present in the hamburger sample.

Alternative Methods of Sample Preparation

Additional methods of meat sample preparation prior to analysis is now described.

Homogenization and Protein Extraction of Meat Samples Using a Bead Homogenizer

After weighing, freezing and grinding meat samples according to previously described methods, lg of each ground meat product is placed in a 20 ml centrifuge tube and 5 stainless steel balls (3 mm) are added. 5 mL of extraction buffer are added to each meat sample. The sample tubes are placed onto a 20 mL tube adaptor and securely fastened. The tubes are then homogenized at Frequency of 70 Hz for 1 minute. The sample tubes are then placed in an ice bath for 1 min. Using a pipette tip with wide bore (e.g., 5 mL pipette tip), aliquot 1.8 mL samples of meat homogenate into labelled, 2-mL microcentrifuge tubes. The total volume of meat homogenate is typically 3-6 mL, and more than one 2-mL microcentrifuge tube is usually needed for each sample. To prepare standard samples, mix the homogenate in a new 2-mL microcentrifuge tube based on the steps previous described. Unknown samples do not need to be mixed at this step. Centrifuge the mixed standard samples at 14,000×g for 15 min. Transfer the clear supernatants (for each sample) into 2-mL microcentrifuge tubes. Transfer 0.4 mL of clear supernatant (collected at into a 2-mL microcentrifuge tube (for each sample). The remaining protein extract can be stored in −20° C. for future use. Add 1.4 mL of 100 mM ammonium bicarbonate to dilute by a factor of 4.5. Rotate the tube up and down to mix well. Prepare the standard and unknowns samples for screening as described previously.

Homogenization and Protein Extraction Using Liquid Nitrogen

After weighing, freezing and grinding meat samples according to previously described methods, 1g of each ground meat product is placed in a ceramic mortar. Add 20 mL of liquid nitrogen. Grind the meat into fine powder carefully with a pestle. Add another 20 mL of liquid nitrogen if liquid nitrogen stops boiling. Transfer the meat powder into a 15 mL centrifuge tube. Add 5 mL of extraction buffer to each meat sample. Shake the mixture for 5 min. using a pipette tip with wide bore (e.g., 5 mL pipette tip), aliquot 1.8 mL samples of meat homogenate into labelled, 2-mL microcentrifuge tubes. The total volume of meat homogenate is typically 3-6 mL, and more than one 2-mL microcentrifuge tube is usually needed for each sample. To prepare standard samples, mix the homogenate in a new 2-mL microcentrifuge tube based on the steps described previously. Unknown samples do not need to be mixed at this step. Centrifuge the mixed standard samples at 14,000×g for 15 min. Transfer the clear supernatants (for each sample) into 2-mL microcentrifuge tubes. Transfer 0.4 mL of clear supernatant into a 2-mL microcentrifuge tube (for each sample). The remaining protein extract can be stored in −20° C. for future use. Add 1.4 mL of 100 mM ammonium bicarbonate to dilute by a factor of 4.5. Rotate the tube up and down to mix well. Prepare the standard and unknowns samples for screening as described previously.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

The invention claimed is:

1. A method of detecting the contamination of a beef sample by one or more meats selected from the group consisting of pork, lamb, chicken and duck, the method comprising:
    adding a proteolytic enzyme to the sample to lyse at least a portion of any of the one or more meats other than beef in the sample, into a plurality of peptides; and
    utilizing liquid chromatography tandem mass spectrometry (LC-MS/MS) to analyze said plurality of peptides to determine whether the one or more meats other than beef is present by monitoring at least one parent-daughter ion pair transition with specified m/z value associated with a specific amino acid sequence selected from the group consisting of:
    i) SEQ ID NO: 1, m/z value of about 453/581 or 453/480; for pork;
    ii) SEQ ID NO: 11, m/z value of about 515/659 or 515/832; or
        SEQ ID NO: 12, m/z value of about 431/589 or 431/862 for lamb;
    iii) SEQ ID NO: 14, m/z value of about 768/923 or 768/1037;
        SEQ ID NO: 16, m/z value of about 684/1136 or 684/1006 for chicken; and
    iv) SEQ ID NO: 17, m/z value of about 677/1122 or 677/992; or
        SEQ ID NO: 18, m/z value of about 977/946 or 977/1442; for duck.

2. The method of claim 1 wherein the proteolytic enzyme comprises trypsin.

3. The method of claim 1 wherein prior to lysing the sample, the sample is prepared by
    a) freezing the sample;
    b) grinding the sample;
    c) extracting proteins of the sample into a extraction solvent, the extraction solvent comprising tris, urea and thiourea;
    d) reducing disulfide bonds in the extracted proteins; and
    e) blocking cysteine and other sulfydryl groups in the reduced proteins.

* * * * *